United States Patent
Heuscher

(10) Patent No.: US 7,042,975 B2
(45) Date of Patent: May 9, 2006

(54) FOUR-DIMENSIONAL HELICAL TOMOGRAPHIC SCANNER

(75) Inventor: Dominic J. Heuscher, Aurora, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 214 days.

(21) Appl. No.: 10/280,734

(22) Filed: Oct. 25, 2002

(65) Prior Publication Data

US 2004/0081270 A1 Apr. 29, 2004

(51) Int. Cl.
*A61B 6/00* (2006.01)

(52) U.S. Cl. .............................. 378/8; 378/144; 378/15
(58) Field of Classification Search .................. 378/144, 378/143, 8, 15, 4, 901
See application file for complete search history.

(56) References Cited

U.S. PATENT DOCUMENTS

| | | | |
|---|---|---|---|
| 4,039,807 A | 8/1977 | Bull | 250/360 |
| 4,182,311 A | 1/1980 | Seppi et al. | 128/653 |
| 5,396,418 A * | 3/1995 | Heuscher | 378/15 |
| 5,744,802 A | 4/1998 | Muehllehner et al. | 250/363.03 |
| 5,960,056 A | 9/1999 | Lai | 378/4 |
| 6,240,157 B1 | 5/2001 | Danielsson | 378/15 |
| 6,539,074 B1 * | 3/2003 | Yavuz et al. | 378/4 |
| 6,583,420 B1 * | 6/2003 | Nelson et al. | 250/397 |
| 6,628,742 B1 * | 9/2003 | Pan et al. | 378/8 |
| 6,760,399 B1 * | 7/2004 | Malamud | 378/9 |
| 2001/0004393 A1 | 6/2001 | Klingenbeck-Regn | 378/19 |
| 2001/0048731 A1 | 12/2001 | Nakamura et al. | 378/4 |

FOREIGN PATENT DOCUMENTS

| | | |
|---|---|---|
| EP | 648 468 | 4/1995 |
| WO | WO 99/18854 | 4/1999 |

* cited by examiner

*Primary Examiner*—Edward J. Glick
*Assistant Examiner*—Elizabeth Keaney
(74) *Attorney, Agent, or Firm*—Fay, Sharpe, Fagan, Minnich & McKee LLP

(57) ABSTRACT

A computed tomography imaging scanner (10) acquires helical cone beam projection data for a volume of interest (46) using at least two source trajectory helices. A reconstruction processor (62) reconstructs the projection data for each helix to generate a corresponding time skewed image representation. A voxel time processor (66) computes an acquisition time for each voxel in each time skewed image representation. A voxel interpolator (68) computes an interpolated voxel value for each voxel based on values of the voxel in the time skewed image representations and corresponding voxel acquisition times. In an electronic embodiment, the computed tomography scanner (10) includes an x-ray source (12) with an axially oriented cylindrical anode (92), an electron source ($96_1$, $96_2$) irradiating the cylindrical anode (92) to produce an x-ray beam (120, 122, 124, 126), and an electron beam deflector (98, 100) that deflects the electron beam along the anode (92) to axially sweep the x-ray beam.

29 Claims, 15 Drawing Sheets

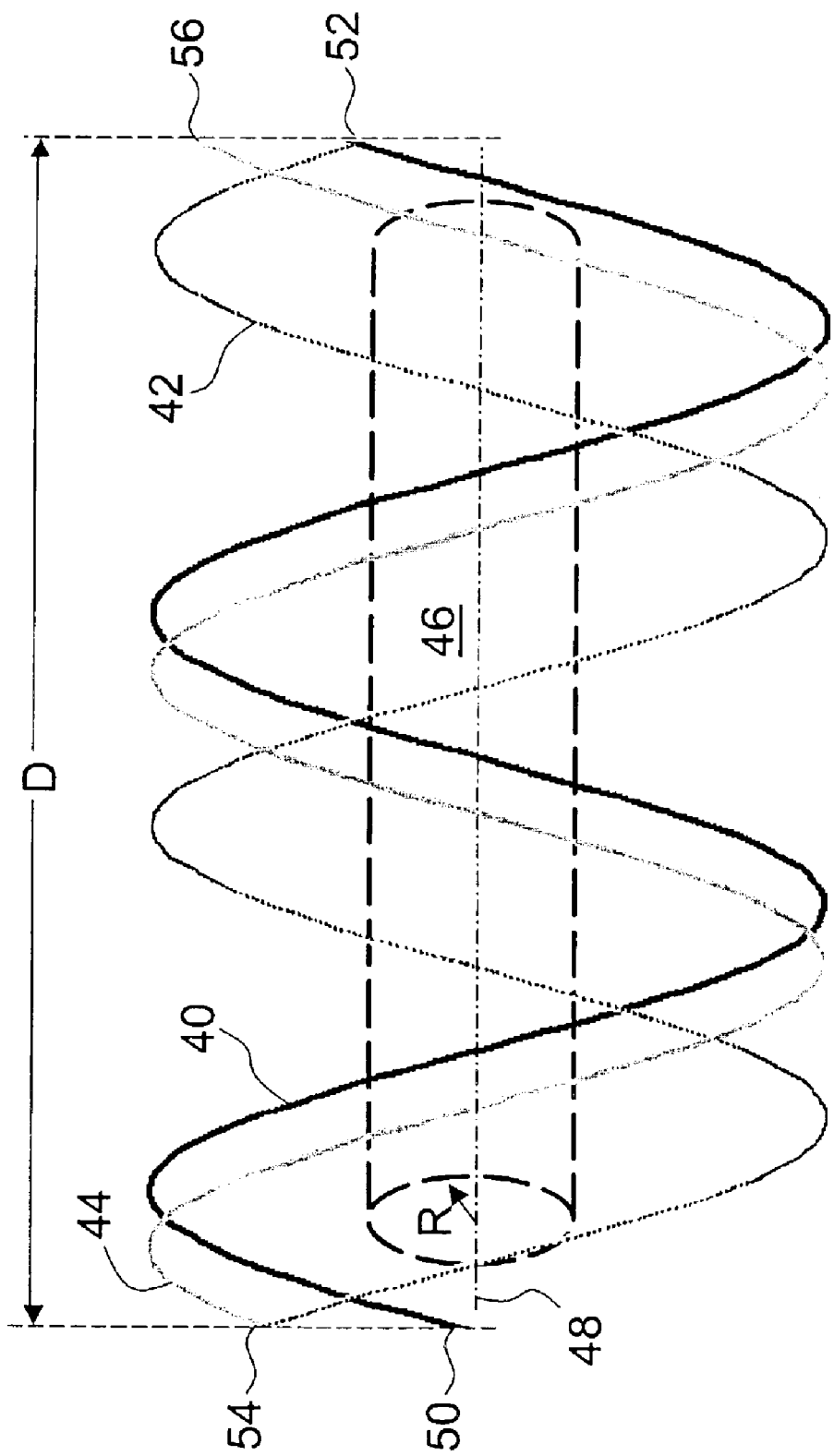

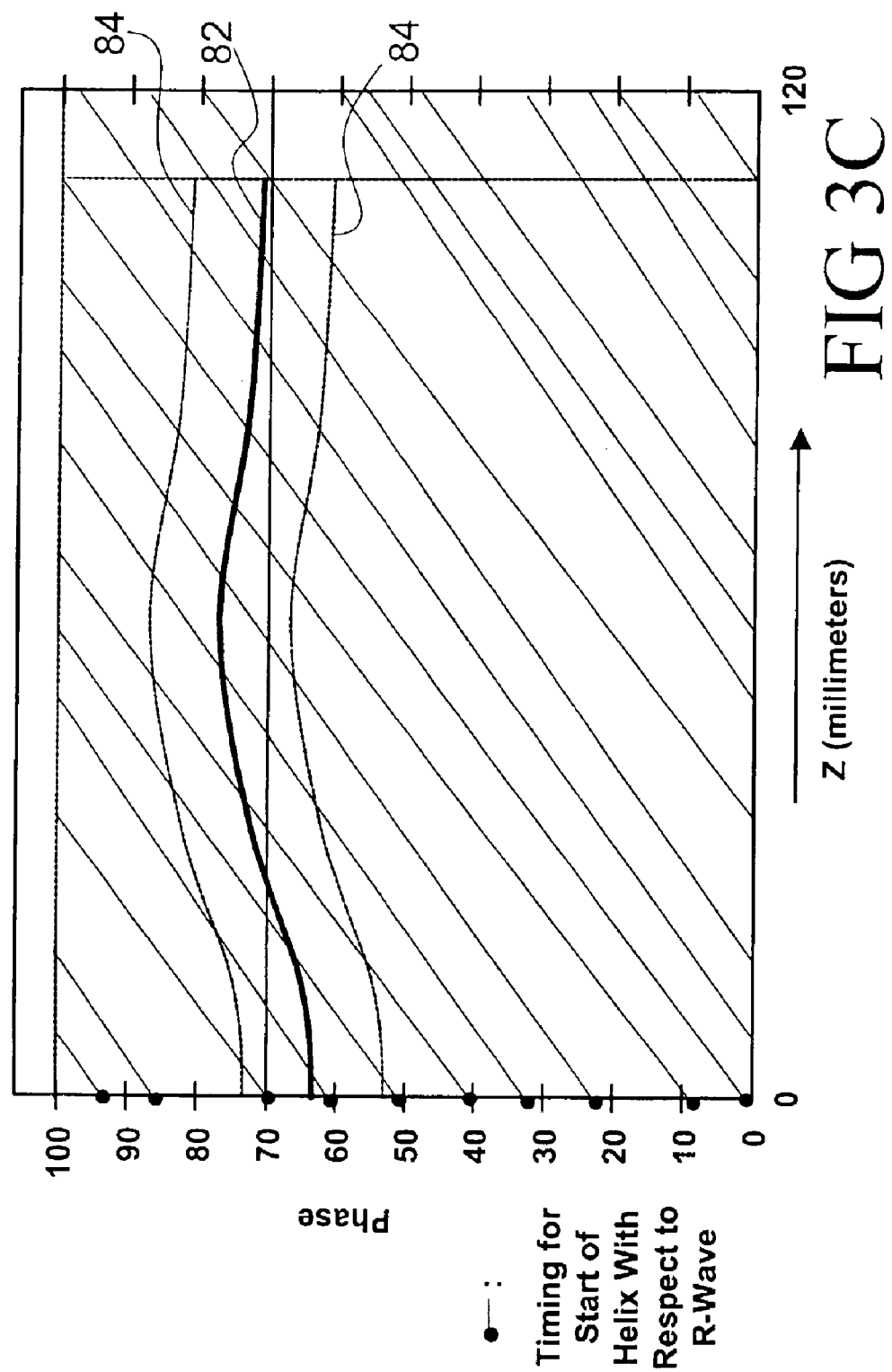

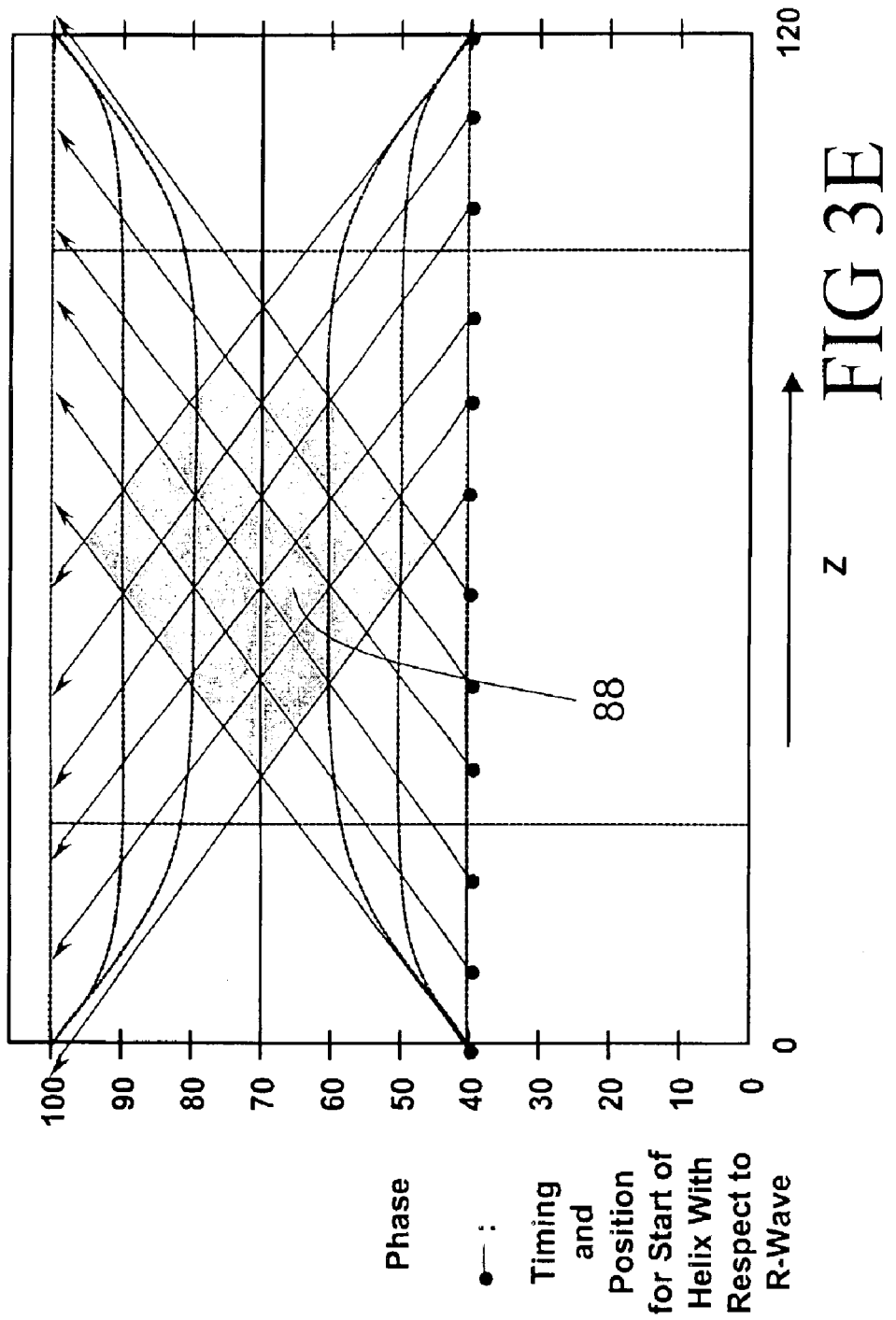

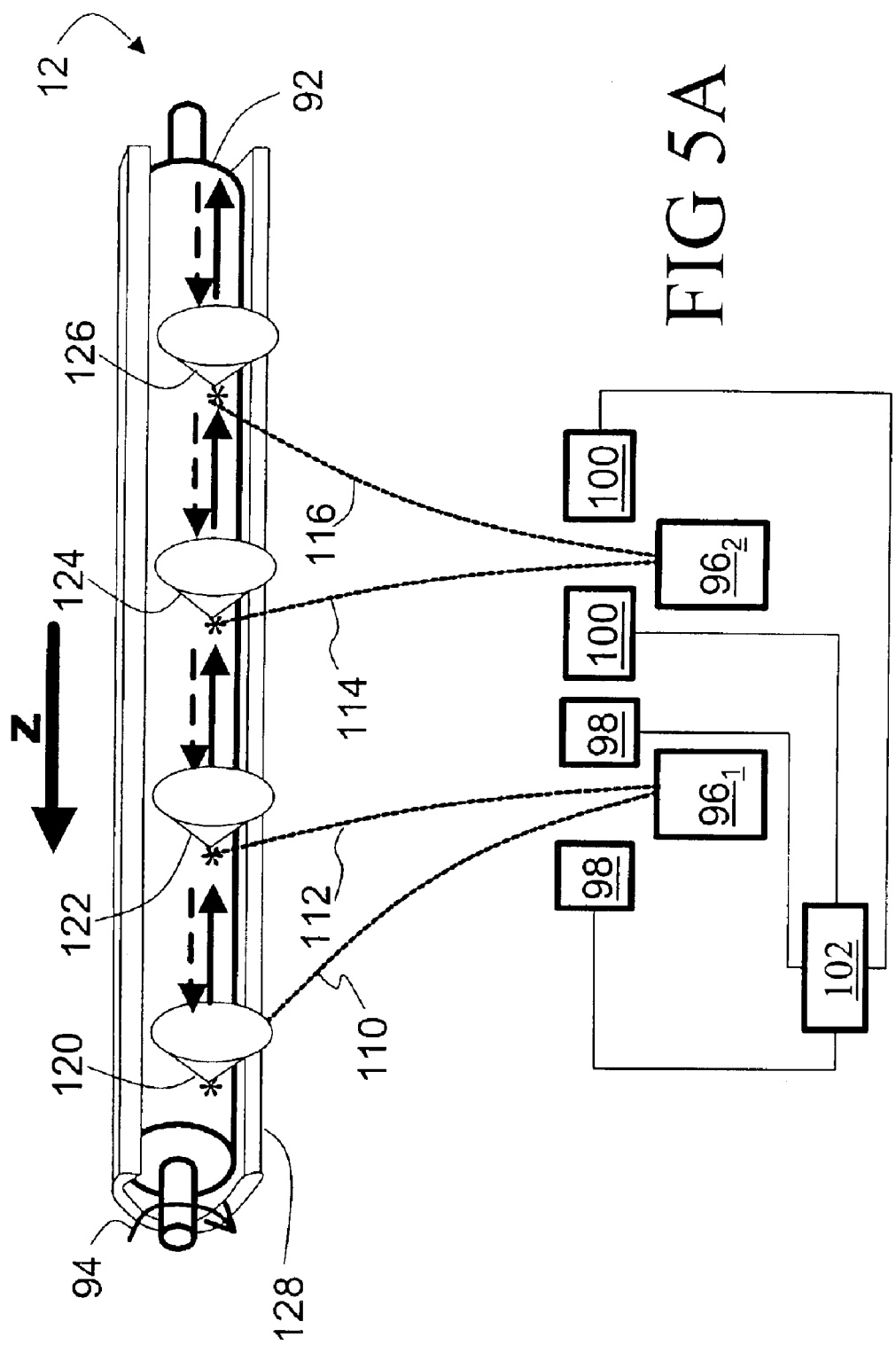

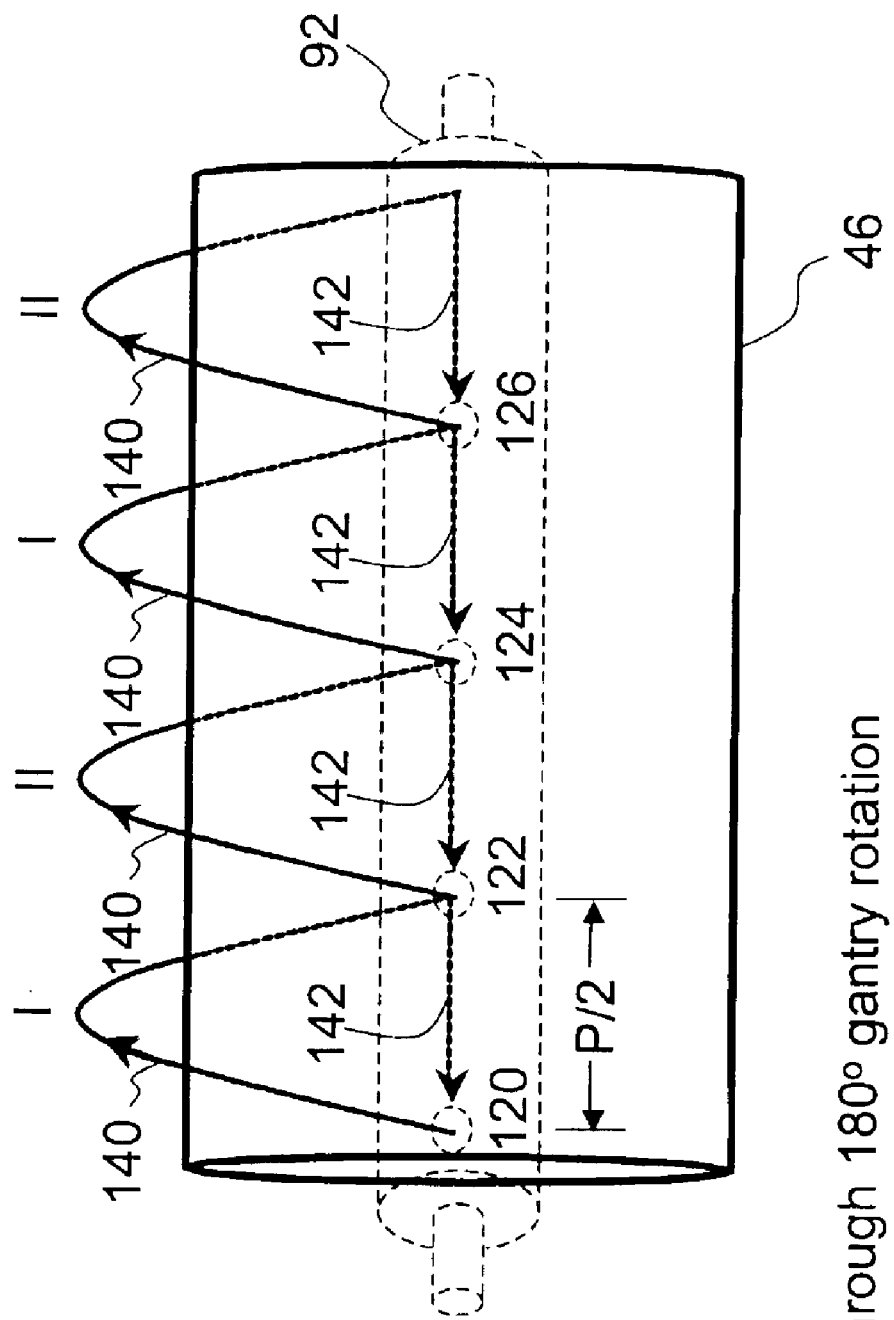

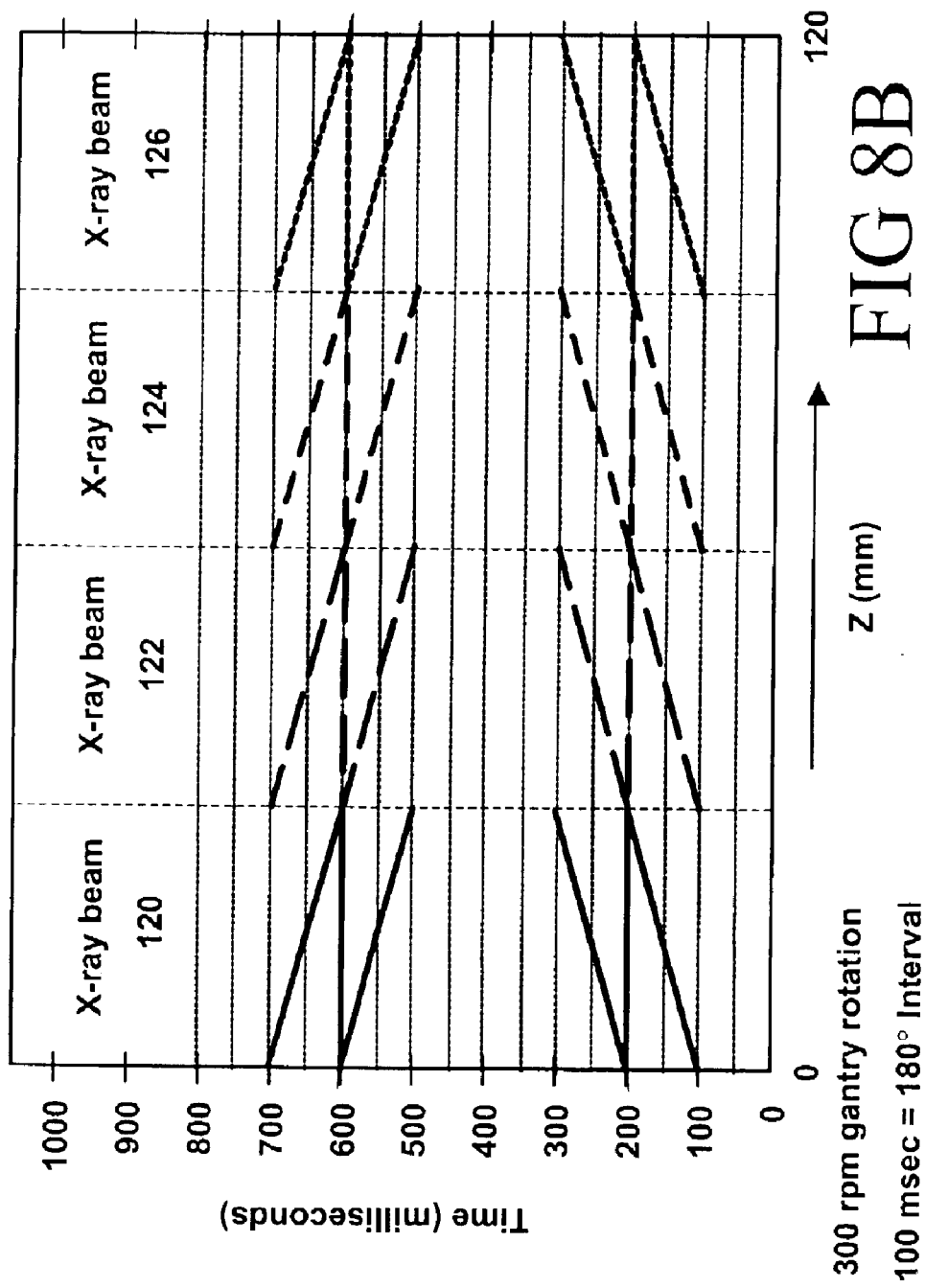

FOUR-DIMENSIONAL HELICAL TOMOGRAPHIC SCANNER

BACKGROUND OF THE INVENTION

The present invention relates to the medical imaging arts. It particularly relates to high-speed and time-dependent helical or multi-slice volumetric cardiac computed tomography (CT) imaging, and will be described with particular reference thereto. However, the invention will also find application in volumetric computed tomographic imaging of other dynamically moving organs, in high resolution contrast agent intake and blood perfusion studies, and the like.

Cardiac computed tomography imaging typically employs an x-ray source that generates a fan-beam, wedge-beam, cone-beam or otherwise-shaped beam of x-rays that traverse an examination region within which a patient's heart is disposed. The cardiac tissue, coronary arteries, and blood interacts with and absorbs a portion of the traversing x-rays. Typically, a contrast agent is administered to the patient to improve blood contrast. A one- or two-dimensional radiation detector arranged opposite the x-ray source detects and measures intensities of the transmitted x-rays.

During scanning the patient is linearly advanced between axial scans to perform multi-slice computed tomography imaging, or the patient is continuously linearly advanced during x-ray source rotation to perform helical computed tomography imaging. The imaging data is reconstructed using a filtered backprojection, a PI reconstruction, or the like to generate volumetric image representations. Preferably, the cardiac cycle is monitored by an electrocardiograph or other device, and the imaging data is binned into cardiac phase bins to reconstruct the heart at a plurality of phases.

A wide range of cardiac studies are performed using cardiac computed tomography imaging. Qualitative review of cardiac computed tomography images by trained medical personnel detects congenital heart defects, large aneurysms or stenoses in the major coronary arteries, and other gross anatomical abnormalities. Analyses such as heart pumping capacity measurements, blood perfusion studies in coronary tissues, and coronary vessel tracking provide complementary quantitative diagnostic information.

In cardiac imaging, problems arise due to a limited temporal resolution of computed tomography, which is controlled by the rotation rate of the x-ray source. To reduce image artifacts, imaging data over at least a half-rotation of the x-ray source (i.e., 180° of data) is preferably acquired for each voxel. At presently achievable gantry rotation rates which are limited by x-ray flux, mechanical stability, and other factors, acquisition of a half-rotation of projection data requires about a tenth of a second or longer. Since the cardiac cycle spans about one second, substantial motion blurring is typically observed.

In cardiac cycle gating, imaging data is acquired using a circular or low-pitch spiral radiation source trajectory such that each voxel remains in the field of view over two or more cardiac cycles. Simultaneously acquired electrocardiographic data is used to select computed tomographic projection data from two or more cardiac cycles that approximately correspond to a selected cardiac phase. The selected data are combined to form a complete data set of about 180° or more for each voxel, and this combined data set is reconstructed to produce an image representation of that cardiac phase.

However, data combined from adjacent cardiac cycles may not readily form a complete data set due to angular redundancies. Synchronizing the rotation with the cardiac cycle to ensure angularly complementary data typically results in sub-optimal computed tomography imaging parameters, for example a reduced gantry rotation rate. Moreover the cardiac cycle can vary during image acquisition, especially in subjects with coronary disease or other cardiac malfunctions.

Another source of error with cardiac gating is inaccuracy in associating the electrocardiographic data with the cardiac cycle. It is known in the art that cardiac motion is only approximately related to the electrocardiographic signal, and that physical motion cycles of the heart components vary non-linearly with variations in the cardiac cycle period, and moreover vary from subject to subject. Particularly in cases of heart arrhythmia where the cardiac cycle period is sometimes variable over a few neighboring heart beats, simple linear scaling of cardiac cycle features with cardiac cycle period is of limited accuracy.

Yet another problem with cardiac gating is that for large volume fields of view the low-pitch spiral takes a substantial length of time to span the volume of interest. This can produce artifacts due to subject motion that vary in an unknown manner along the axial direction. Alternatively, a large-area beam and corresponding large-area detector can be employed to enable use of a larger spiral pitch. However, this increases system cost, and image artifacts can occur due to spatial non-uniformity of the large-area beam or detector.

The present invention contemplates an improved apparatus and method that overcomes the aforementioned limitations and others.

SUMMARY OF THE INVENTION

According to one aspect of the invention, a helical cone beam computed tomography imaging method is provided. Helical cone beam computed tomography projection data is acquired for a volume of interest using a plurality of source trajectory helices. The acquired helical cone beam computed tomography projection data for each helix are reconstructed to generate a corresponding time skewed volume image representation of the volume of interest. For each time skewed volume image representation, a voxel acquisition time is computed for each voxel. For each voxel, an interpolated voxel value is computed based on values of the voxel in the plurality of image representations and corresponding voxel acquisition times.

According to another aspect of the invention, an apparatus is disclosed for performing helical cone beam computed tomography imaging. A means is provided for acquiring helical cone beam computed tomography projection data for a volume of interest using a plurality of source trajectory helices. A means is provided for reconstructing the acquired helical cone beam computed tomography projection data for each helix to generate a corresponding time skewed volume image representation of the volume of interest. A means is provided for computing a voxel acquisition time for each voxel of each time skewed image representation. A means is provided for computing an interpolated voxel value for each voxel based on values of the voxel in the plurality of time skewed image representations and corresponding voxel acquisition times.

According to yet another aspect of the invention, an apparatus is disclosed for performing high-speed computed tomography imaging. An x-ray source is disposed on a rotating gantry and rotates therewith. The x-ray source includes an axially oriented cylindrical anode, an electron source irradiating the cylindrical anode to produce an x-ray beam traversing a volume of interest, and an electron beam deflector that axially deflects the electron beam along the cylindrical anode to axially sweep the x-ray beam. The deflector cooperates with the rotating gantry to produce a helical trajectory of the x-ray beam about the volume of interest. A radiation detector is arranged to measure the x-ray beam after passing through the volume of interest. A reconstruction processor reconstructs the acquired projection data to produce a time skewed image representation corresponding to the helical trajectory.

According to still yet another aspect of the invention, an x-ray tube is disclosed, including a cylindrical anode whose cylindrical axis is axially oriented. An electron source produces an electron beam generally directed toward the cylindrical anode. The electron beam interacts with the cylindrical anode to produce x-rays. An electron beam deflector sweeps the electron beam axially across the cylindrical anode.

One advantage of the present invention resides in increased reconstruction accuracy compared with conventional cardiac gating employing circular or low-pitch spiral orbits. The improved accuracy is particularly apparent for large volumes of interest.

Another advantage of the present invention resides in improved temporal resolution at the voxel level.

Yet another advantage of the present invention resides in reduced sensitivity to heart arrhythmia through the use of a large-pitch spiral source trajectory that substantially spans the volume of interest in about one cardiac cycle period or less.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various process operations and arrangements of process operations. The drawings are only for the purpose of illustrating preferred embodiments and are not to be construed as limiting the invention.

FIG. 2 shows an exemplary three interlaced helical trajectories generated by cyclic relative axial motion of the x-ray tube and the volume of interest.

FIG. 3C shows a cardiac phase-axial position map of projection data acquired using ten helices initiated at cardiac percentage phase intervals adjusted to compensate for variations in the heart rate to improve a constructed 70% cardiac phase.

FIG. 3E shows a cardiac phase-axial position map of projection data acquired using twelve helices each initiated at a 40% cardiac percentage phase, the helices being performed in a bi-directional or back-and-forth fashion.

FIG. 5A shows a preferred embodiment of an x-ray tube that provides for electronic axial sweeping of an x-ray beam and/or axial switching between a plurality of axially spaced x-ray beams.

FIG. 6A shows first helical half-turns acquired during a first 180° gantry rotation using switched x-ray beams that are axially swept across the cylindrical anode of the x-ray tube of FIGS. 5A and 5B.

FIG. 8B shows a map of projection data acquisition time versus axial position for sampling performed in alternating axial directions using the electronically switched/swept x-ray beam embodiment of FIGS. 5–7.

DETAILED DESCRIPTION OF THE PREFERRED EMBODIMENTS

Figure 1:
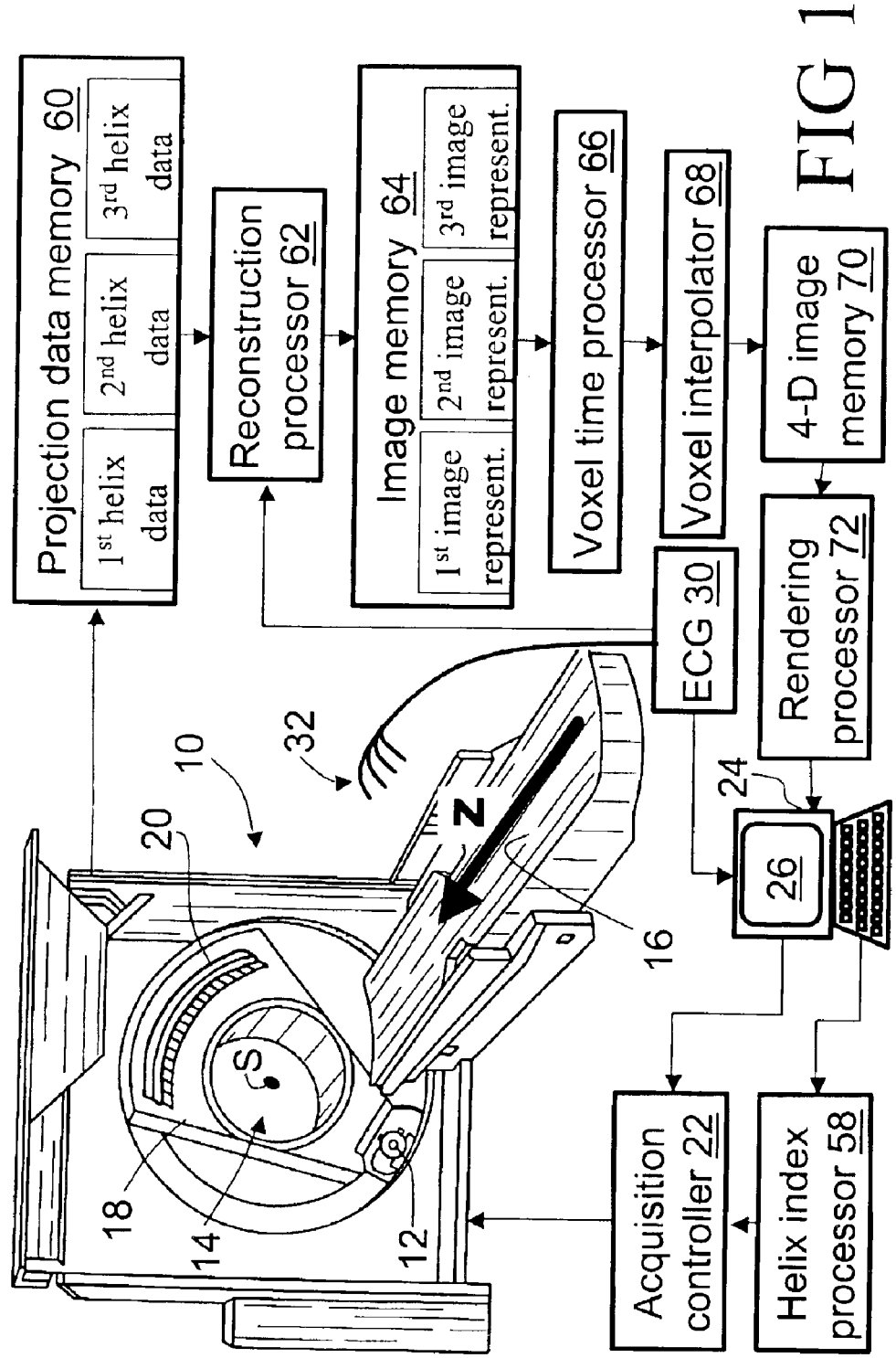
FIG. 1 shows an exemplary four-dimensional helical computed tomography imaging apparatus for performing four-dimensional cardiac imaging.

With reference to FIG. 1, a computed tomography (CT) imaging scanner 10 includes an x-ray source 12 that produces a fan-shaped, cone-shaped, wedge-shaped, or otherwise-shaped x-ray beam directed into an examination region 14 which contains an imaging subject (not shown) arranged on a subject support 16. For cardiac imaging, a patient is positioned with the subject heart substantially centered within the examination region 14. The subject support 16 is linearly movable in a Z-direction while the x-ray source 12 is mounted on a rotating gantry 18 that rotates around the Z-axis.

In a mechanical computed tomography imaging embodiment, the rotating gantry 18 rotates simultaneously with linear advancement of the subject support 16 to produce a generally helical trajectory of the x-ray source 12 about the examination region 14. In an electronic operating embodiment, the subject support 16 remains stationary and the x-ray source 12 electronically sweeps the x-ray beam axially across the examination region 14 during gantry rotation. The x-ray source 12 preferably produces a wedge- or cone-shaped x-ray beam that diverges in the imaging plane and in the Z-direction.

An x-ray detector 20 is arranged on the gantry 18 across from the x-ray source 12. The x-ray detector 20 preferably includes several rows of detectors along the Z-direction for simultaneously acquiring imaging data along a portion of the Z-direction in each projection view. The x-ray detector 20 is arranged on the rotating gantry 18 opposite to the x-ray source 12 and rotates therewith so that the x-ray detector 20 receives x-rays that traverse the examination region 14 as the rotating gantry 18 rotates. Instead of the arrangement shown in FIG. 1, it is also contemplated to arrange the x-ray detector on a stationary gantry encircling the rotating gantry such that the x-rays continuously impinge upon a continuously shifting angular portion of the radiation detector during x-ray source rotation.

A computed tomography imaging data acquisition controller 22 controls the scanner 10 to perform selected imaging operations using helical trajectories of the x-ray source 12 relative to the subject. The helical trajectories can be accomplished by gantry rotation in cooperation with relative mechanical axial motion of the x-ray tube 12 and the subject support 16, or by gantry rotation in cooperation with electronic axial motion of the x-ray beam. A user interface device 24, which is typically a personal computer, workstation, or other computer device, communicates with the acquisition controller 22 to allow a user to construct, select, initiate, monitor, or otherwise supervise a selected imaging session. The user interface device 24 preferably includes a graphical display 26.

In cardiac computed tomography imaging, a contrast agent is preferably administered to the patient to selectively improve x-ray contrast of the blood. For steady state studies, the contrast agent is preferably administered as an intravenous drip at a steady state rate to provide a generally steady state x-ray contrast for cardiac computed tomography imaging. For perfusion studies or contrast agent intake studies, a bolus injection of the contrast agent is administered, in which a substantial quantity of contrast agent is rapidly intravenously injected. In some types of cardiac imaging, the contrast agent is optionally omitted.

Cardiac computed tomography imaging also typically employs a device for monitoring the cardiac cycle. This device is typically an electrocardiograph (ECG) 30, although an ultrasonic imaging device or other device can also be used. As is known in the art, the electrocardiograph 30 includes a plurality of electrical leads 32 that contact the subject's chest to detect electrical signals associated with the cardiac cycle.

Although cardiac imaging is particularly described herein, it should be appreciated that the imaging can pertain to other types of cyclical temporal variations in a patient or other subject. Moreover, the imaging can pertain to non-cyclical temporal variations in the subject, such as contrast agent intake studies.

With continuing reference to FIG. 1 and with further reference to FIG. 2, in a mechanical embodiment of four-dimensional helical computed tomographic imaging, the acquisition controller 22 performs a plurality of large-pitch helical scans or source trajectories 40, 42, 44 that quickly cover a volume of interest 46 defined by an imaging subject such as a heart. For convenience in computing various imaging parameters, a cylindrical volume of interest 46 having a central cylindrical axis 48 is shown. In a suitable mechanical embodiment, the plurality of source trajectories 40, 42, 44 are acquired by moving the subject volume of interest 46 on the subject support 16 back and forth a selected distance D along the axial or Z-direction while the gantry 18 and x-ray source 12 rotate. For cardiac imaging, each source trajectory helix 40, 42, 44 preferably covers the cardiac volume of interest 46 in a time interval that is less than about one cardiac cycle in length.

The first helix 40 is generated by relative movement of the source 12 and the volume of interest 46 in a +Z-direction. The source trajectory helix 40 initiates at a starting point 50 and terminates at a point 52.

The second helix 42 initiates at the point 52 at the same angular coordinate as the first trajectory helix 40 terminated at. However, the second helix 42 is generated by relative movement of the source 12 and the volume of interest 46 in a −Z-direction. The second helix 42 terminates at a point 54.

The third helix 44 initiates at the point 54 at the same angular coordinate as the second trajectory helix 42 terminated at. The third helix 44 is generated by relative movement of the source 12 and the volume of interest 46 in a +Z-direction. The third trajectory 44 terminates at a point 56.

Optionally, additional trajectories can be generated by continuing the back and forth relative axial motion of the source 12 and the volume of interest 46. It will also be appreciated that only two trajectories can be employed. Furthermore, it will be appreciated that in an alternative embodiment, the scans can all occur in the same direction, for example in the +Z-direction, with the subject support 16 returning to its initial position before each scan in the +Z-direction.

Moreover, although the helices 40, 42, 44 are temporally continuous, that is, each helical trajectory starts substantially immediately upon termination of the previous trajectory, it is also contemplated to include a delay between helices. For example, initiation of each trajectory helix is optionally triggered by a selected signal from the electrocardiograph 30 such that the plurality of helices span the cardiac cycle.

Preferably, each helix 40, 42, 44 is acquired in one cardiac cycle period or less. For a cardiac volume of interest 46 such as a heart which is typically about twelve centimeters along the axial or Z-direction, the helical trajectories 40, 42, 44 are large-pitch helical trajectories. The x-ray source 12 produces a conical- or wedge-shaped beam which is collimated to have a divergence in the axial or Z-direction and a helical source trajectory pitch such that for each trajectory 40, 42, 44 each voxel in the volume of interest 46 remains within the field of view for about 180° or more of angular rotation of the source 12. This provides sufficient angular data to accurately reconstruct the voxel.

With particular reference returning to FIG. 1, a helix index processor 58 communicates with the acquisition controller 22 to specify and index the several helices 40, 42, 44. A projection data memory 60 stores projection data of the first, second, and third helices 40, 42, 44 in corresponding data bins. A reconstruction processor 62 reconstructs projection data of each of the helices 40, 42, 44 to produce corresponding image representations that are stored in an image memory 64. As discussed below, each of the image representations reconstructed from one of the helices 40, 42, 44 is time skewed since projection data for voxels axially located near the end of the helix are acquired later than projection data for voxels axially located near the beginning of the helix.

Each image voxel of each image representation is acquired from angularly contiguous projection data acquired over an angular interval during which the voxel remains within the field of view. For a helical pitch selected such that a voxel located on the central cylindrical axis 48 remains in the field of view for an angular interval of 180°, the angular viewing interval for a voxel lying a distance R away from the central axis 48 lies within a range of angular intervals bounded by:

$$\Delta\theta_{r,\theta,z} = \pi \pm \sin^{-1}\left(\frac{R}{S}\right), \quad (1)$$

where S is a distance between the radiation source 12 and an isocenter S of the examination region 14 and $\Delta\theta_{r,\theta,z}$ is the maximum and minimum angular interval (for the "+" and "−" options, respectively, of the "±" operator) during which the voxel at R remains in the field of view. For example, for R=15 cm and S=57 cm, $\Delta\theta_{r,\theta,z}$ is in the range of 164° to 195°.

The angular interval bounds $\Delta\theta_{r,\theta,z}$ correspond to temporal viewing interval bounds, that is, temporal resolution bounds, given by:

$$\text{Temporal resolution} = \frac{T_{rot} \cdot \Delta\theta_{r,\theta,z}}{2\pi}, \quad (2)$$

where $T_{rot}$ is the time period for a 360° rotation of the x-ray source 12. For R=15 cm and S=57 cm, and $T_{rot}$=0.4 sec (rotation rate=150 rpm) the temporal resolution of each voxel lies in a range of 0.183 sec to 0.217 sec.

Although the equation (2) gives bounds for the temporal resolution of each voxel of the image representations that are stored in an image memory 64, the overall image is acquired over a substantially longer period. For example, in FIG. 2 each trajectory 40, 42, 44 spans about 850° and is therefore acquired (for $T_{rot}$=0.4 sec) over about 0.95 sec. The three scans collectively are acquired over about 2.8 sec. As a result, there is a substantial time skew of the voxels making up the image representations.

With continuing reference to FIGS. 1 and 2, to account for the time skew a voxel time processor 66 computes a voxel acquisition time for each voxel. In a preferred embodiment, this computation is based on the PI-line corresponding to each voxel. As is known in the art, the PI-line intersects the voxel and the two nearest points along the corresponding helical trajectory 40, 42, 44. These two nearest points are designated herein as angles $\theta_1$ and $\theta_2$ (where the beginning of the scan is taken as θ=0° and the scan progresses in a positive angular direction). Since the voxel is reconstructed from projection data acquired during the contiguous angular interval [$\theta_1$, $\theta_2$] corresponding to a contiguous temporal interval, an average or mean angle $\theta_{avg}$ at which the projection data for the voxel was acquired is given by:

$$\theta_{avg} = \frac{\theta_1 + \theta_2}{2}. \quad (3)$$

The mean angle $\theta_{avg}$ corresponds to a mean or average time for the voxel acquisition given by:

$$\text{Voxel time} = \frac{T_{rot} \cdot \theta_{avg}}{2\pi} + T_o, \quad (4)$$

where $T_o$ is the time for θ=0°, that is, the time when the helical trajectory was initiated. The voxel acquisition time given by equations (3) and (4) is preferably computed by the voxel time processor 66.

A substantial time skew exists between slices along the axial or Z-direction. However, even within an axial slice the voxels will be time skewed and have differing voxel acquisition times due to differences in the contiguous angular interval [$\theta_1$, $\theta_2$] of the corresponding PI lines. It will be recognized that the contiguous angular viewing intervals [$\theta_1$, $\theta_2$] for the voxels are determined by the reconstruction processor 62 as part of the usual cone beam image reconstruction process.

In addition to a voxel acquisition time, each voxel also has a value, such as a gray scale intensity value, in each of the time skewed image representations. As each such voxel value was acquired at about the corresponding voxel acquisition time, a time-dependent voxel value is readily computed using interpolation, curve fitting, or another method by a voxel interpolator 68. The time-dependent voxel values for the voxels comprising the volume of interest 46 define a four-dimensional image representation over the volume of interest 46 and the acquisition interval of the several trajectories 40, 42, 44. The four-dimensional image representation is stored in a four-dimensional image memory 70.

Alternatively, an image of the volume of interest 46 at a selected time is generated by selecting voxels whose voxel acquisition time corresponds to the selected time. Preferably, two or more voxel values with voxel acquisition times near the selected time are interpolated, curve-fitted, or otherwise combined by the voxel interpolator 68 to estimate the value of the voxel at the selected time. By performing such interpolation for each voxel in the volume of interest 46, an image representation corresponding to the selected time with improved temporal resolution is obtained.

The four-dimensional image representation or the image representation at the selected time is preferably processed by a rendering processor 72 which produces a three-dimensional rendering for the selected time, image projections or slices at the selected time, a temporal sequence of image projections or slices, a cinematic (CINE) sequence for the imaged volume over the imaging interval, or the like, which is displayed on the graphical display 26 of the user interface device 24.

For cardiac imaging, each helical trajectory or scan is preferably gated based on the cardiac cycling information provided by the electrocardiograph 30 to sample all cardiac cycle phases of interest. If each helix is initiated at a different phase of the cardiac cycle, for example by gating initiation of each trajectory, then for N scans a corresponding N cardiac phases can be reconstructed. The value N is given by:

$$N = \frac{T_{cc}}{0.25 \cdot T_{rot}} = \frac{240}{HR \cdot T_{rot}} \quad (5)$$

where $T_{rot}$ is the time period for a 360° rotation of the x-ray source 12 in seconds, $T_{cc}$ is the cardiac cycle period in seconds, and HR is the heart rate in beats per minute.

For example, if HR=60 beats per minute and $T_{rot}$=0.4 sec (radiation source rotation rate=150 rpm) then N=10. That is, if ten trajectories or scans are acquired each starting at a different cardiac phase, then ten cardiac phases can be resolved.

With continuing reference to FIG. 2, the helical trajectories 40, 42, 44 are acquired using a cyclical axial mechanical movement of one of the subject support and the radiation source. In this mechanical embodiment, and for presently achievable fields of view and source rotation rates, imaging a volume of interest 46 that extends axially about twelve centimeters, such as a heart, typically requires about a second or longer. Correspondingly, anatomical motions should exceed about one second to be tracked.

By employing cardiac gating, however, cyclical cardiac motions can be tracked by acquiring a number of helix scans corresponding to the number of cardiac phases to be resolved. The images corresponding to the several helix scans are optionally relatively spatially registered using nominally stationary image features such as the chest walls, to correct for patient motion or other motion artifacts on time scales of around the helical scan time.

A cardiac phase or state of motion is selected, and voxels of the time skewed image representations whose acquisition times are close to occurrences of the selected cardiac phase or state of motion are identified based on the cardiac cycling information provided by the electrocardiograph 30. Optionally, a physiological model of the cardiac motion is used to more precisely identify a time occurrence of the selected state of cardiac motion from the electrocardiographic data. The identified voxels are temporally interpolated, averaged, or otherwise combined to compute an image representation of the selected cardiac phase or state of motion which spans the volume of interest. Such an image representation can be computed from the time skewed image representations for each resolvable cardiac phase.

Figure 3A:
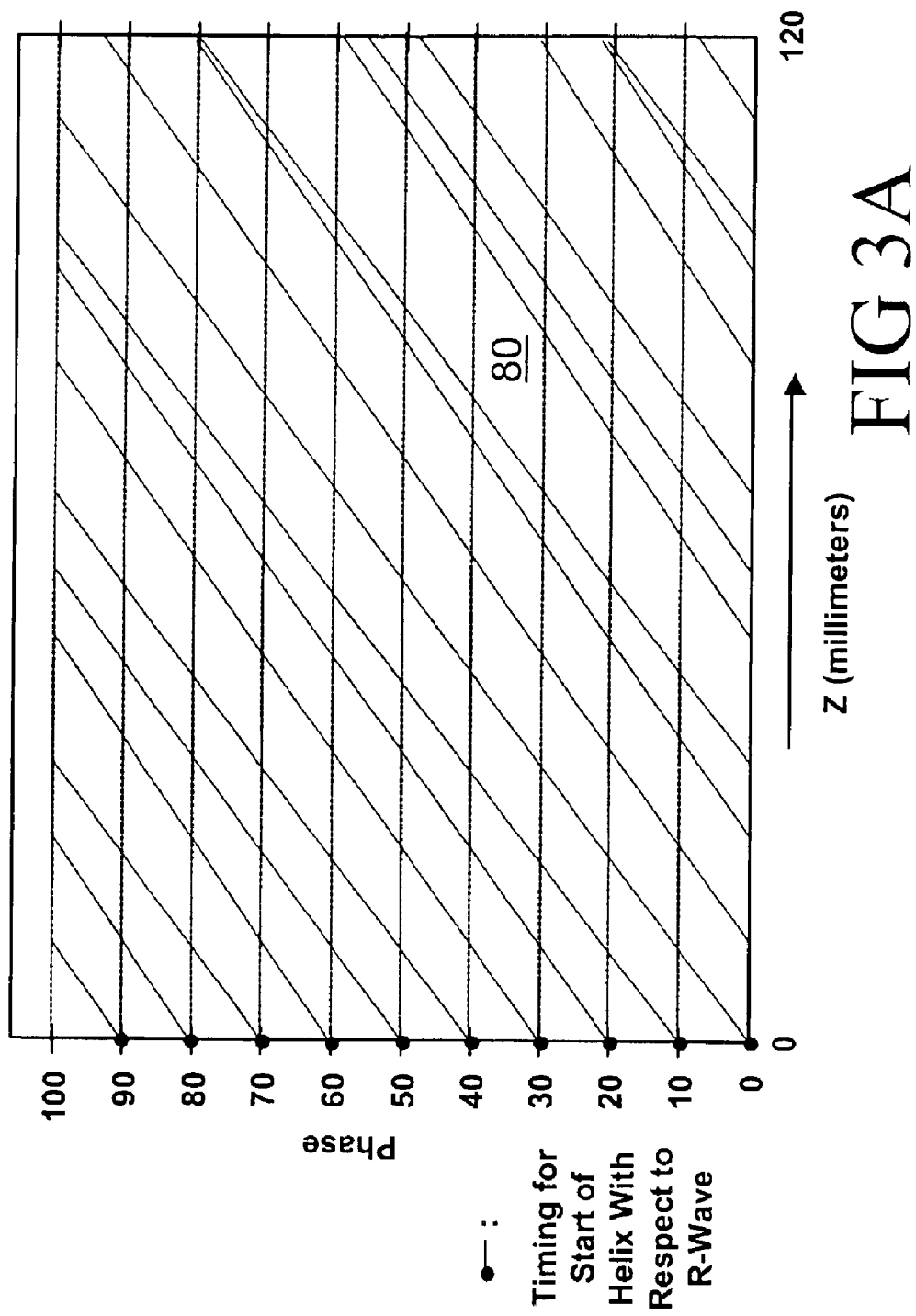
FIG. 3A shows a cardiac phase-axial position map of projection data acquired using ten helices initiated at evenly spaced cardiac percentage phase intervals, and interpolative constructing of ten cardiac phase image representations therefrom.

For example, with reference to FIG. 3A a cardiac phase-axial position map of projection data acquired using ten helices initiated at evenly spaced cardiac percentage phase intervals is simulated. Helices are successively initiated at axial position z=0 via cardiac gating at each of 0%, 10%, 20%, 30%, 40%, 50%, 60%, 70%, 80%, and 90% of the cardiac cycle. The initiation of each scan is represented by a filled circle.

The acquired projection data are represented by slanted lines extending from the initiation times. The slanted lines represent the progression of cardiac phase as the helical trajectory simultaneously progresses along the axial or z-direction. A time skewed image representation is reconstructed using projection data acquired during each of the ten helices, and interpolated voxels are selectively computed for each of the ten cardiac percentage phases 0%, 10%, 20%, 30%, 40%, 50%, 60%, 70%, 80%, and 90%. Such interpolation is performed throughout the volume of interest, and the resultant interpolated images of the cardiac phases 0% (equivalent to 100%), 10%, 20%, 30%, 40%, 50%, 60%, 70%, 80%, and 90% are represented by horizontal dotted lines in FIG. 3A.

As seen in FIG. 3A, there is some non-uniformity in the available data for each selected cardiac phase due to heart rate variations occurring during the acquisition time of the ten helices. For example, a region 80 has widely spaced sampling. Variations in the heart rate manifest in FIG. 3A as variations in the slopes of the slanted lines representing the acquired projection data.

Figure 3B:
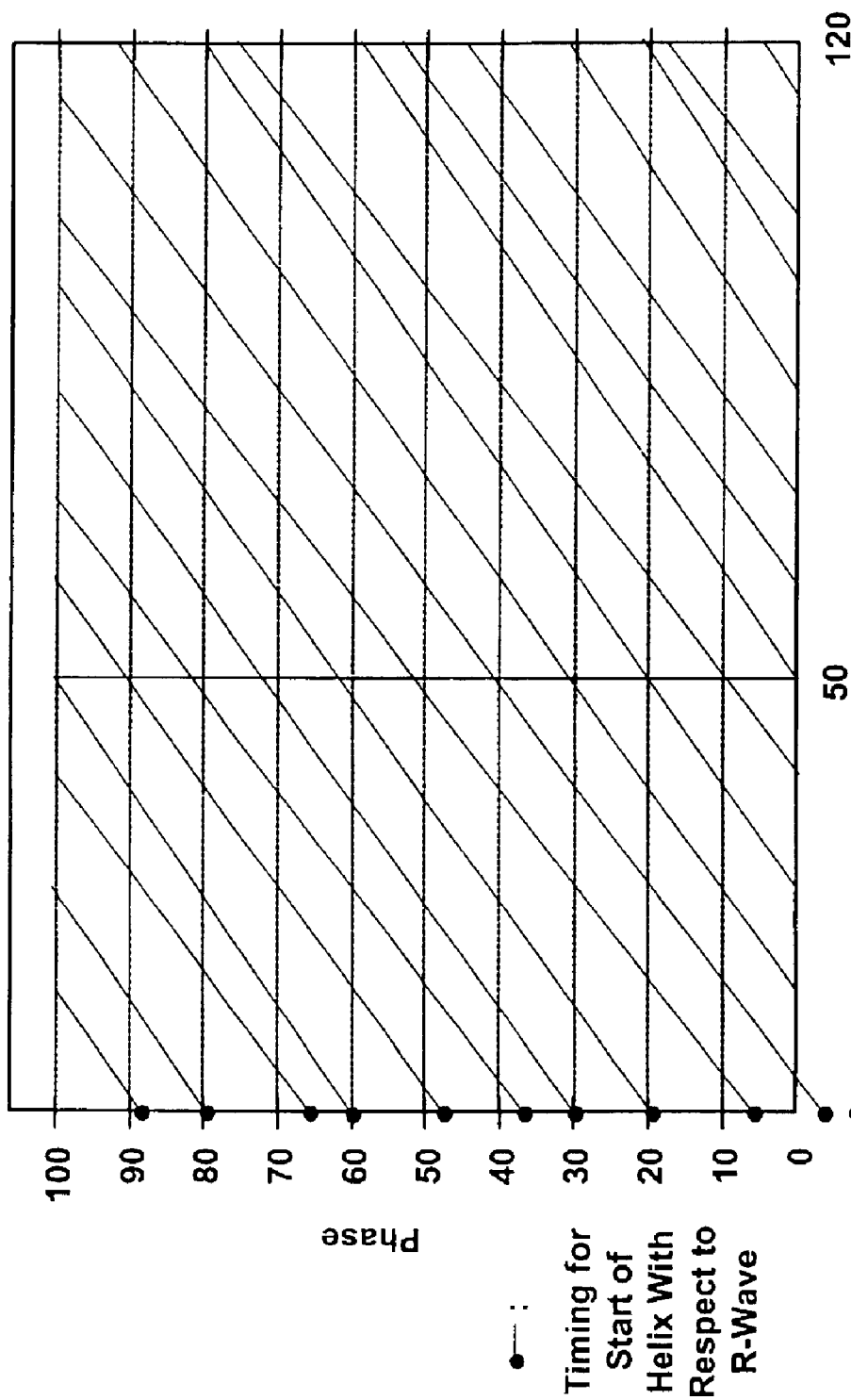
FIG. 3B shows a cardiac phase-axial position map of projection data acquired using ten helices initiated at cardiac percentage phase intervals adjusted to compensate for variations in the heart rate such that a constructed slice at z=50 is sampled at substantially uniformly spaced cardiac phases.

With reference to FIG. 3B, the cardiac gating is adjusted to compensate for changes in the heart rate detected by the electrocardiograph 30, with the objective of obtaining imaging data at uniform cardiac percentage phase intervals for an axial slice at z=50 (represented by a dark vertical line at z=50). It will be seen in FIG. 3B that the projection view samples at z=50 are substantially uniformly spaced in cardiac phase.

With reference to FIG. 3C, the cardiac gating is adjusted to compensate for changes in the heart rate, with the objective of obtaining spatially uniform sampling at a cardiac state near the 70% cardiac phase. The cardiac state of interest is represented by a solid generally horizontal curved line 82. The cardiac state 82 can be, for example, a state of minimum cardiac motion, which minimum occurs at somewhat different cardiac phases for along the axial or Z-direction. Similar adjacent phases are indicated by dotted generally horizontal curved lines 84 and can also be reconstructed.

Figure 3D:
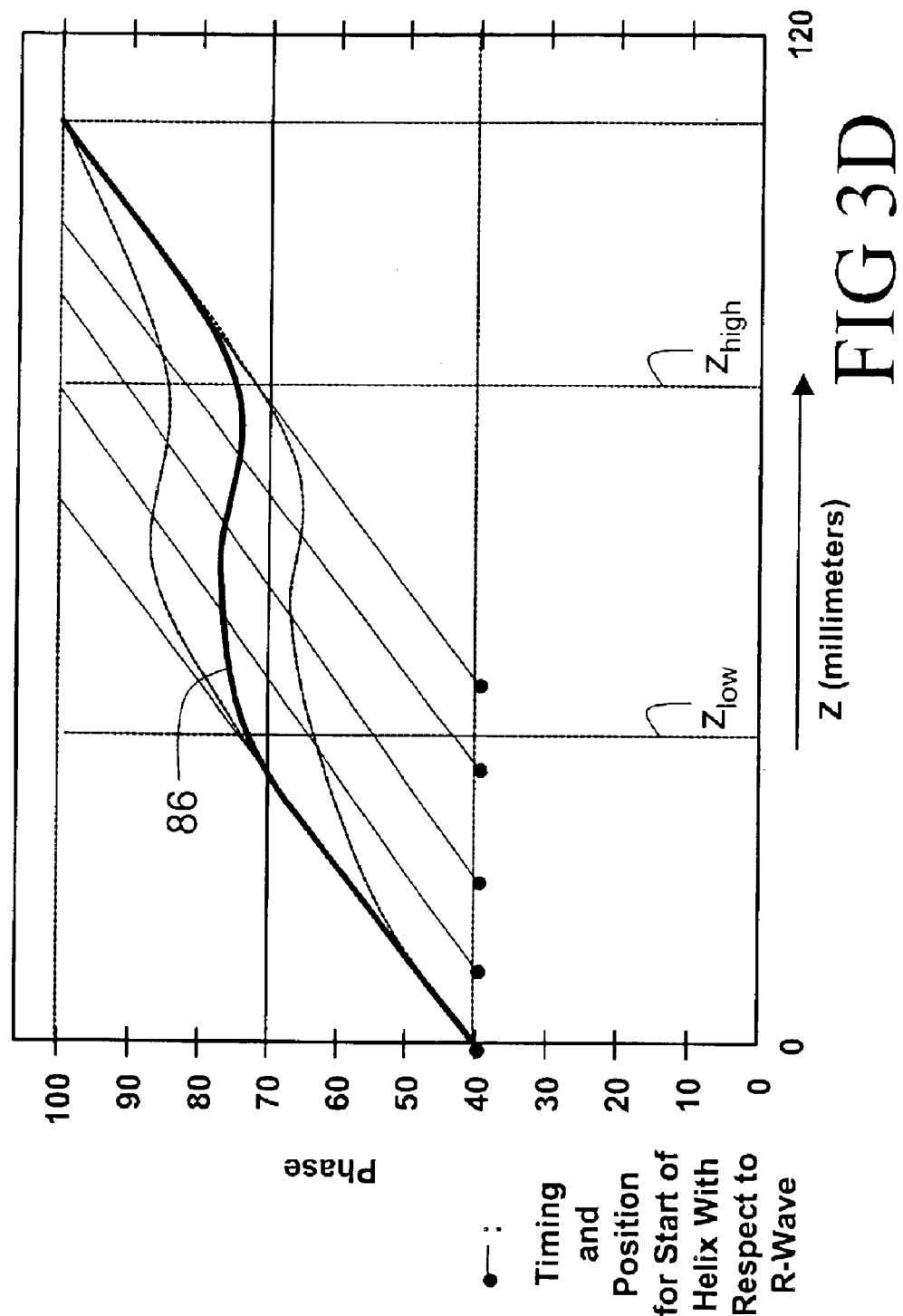
FIG. 3D shows a cardiac phase-axial position map of projection data acquired using five helices each initiated at a 40% cardiac percentage phase with starting axial positions selected to particularly target imaging of a 70% cardiac phase over an axial interval $[z_{low}, z_{high}]$.

With reference to FIG. 3D, imaging of a cardiac state 86 near the 70% cardiac phase over a range $[z_{low}, z_{high}]$ is performed. Each helix is started at a percentage cardiac phase of 40%, and projection data is acquired between 40% and 100% cardiac phase. Preferably, the x-ray beam is shuttered during the cardiac phase interval 0%–40% to reduce the radiation dose delivered to the patient. Only five such dose-modulated helices are sufficient to provide substantially spatially uniform sampling across the $[z_{low}, z_{high}]$ range. Moreover, the five helices provide imaging data extending across the full volume of interest (z=0 through z=120), albeit at different cardiac phases. This spatially extended imaging data can be used, for example, to perform image registration using relatively stationary imaged features such as chest walls.

With reference to FIG. 3E, a bi-directional or back-and-forth axial cycling is employed to provide high resolution imaging data over a diamond-shaped region 88 and lower resolution throughout the volume of interest using twelve helical scans, six in the +Z-direction and six in the −Z-direction. Each scan spans the cardiac phase range 40%–100%, and again dose modulation is preferably performed by shuttering the x-ray beam in the 0%–40% cardiac phase range. The bi-directional imaging of FIG. 3E provides redundant projection imaging data at crossing points of the +Z-direction and the −Z-direction scans. Dotted generally horizontal lines in FIG. 3E show suitable cardiac state images interpolated from the acquired projection views.

Figure 4:
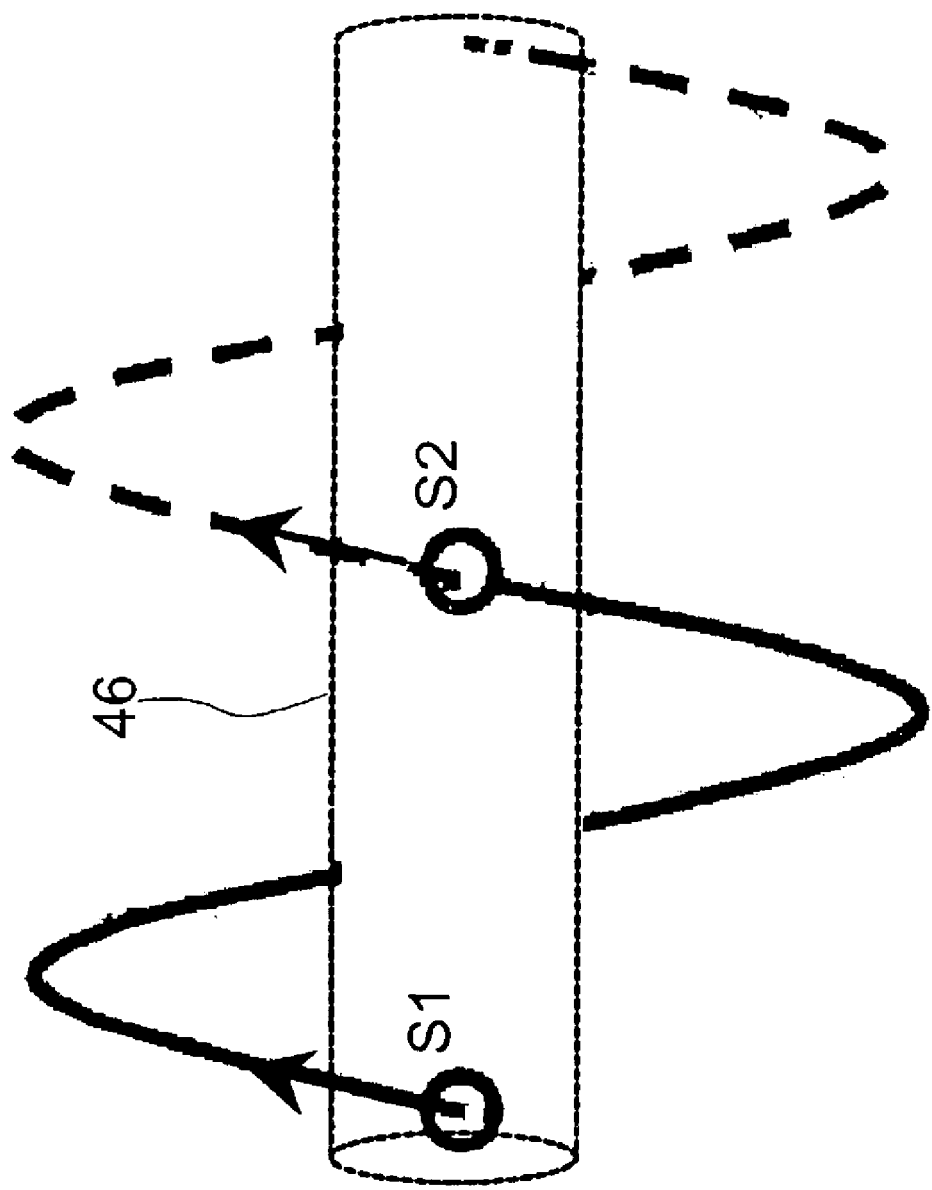
FIG. 4 shows an exemplary a helical trajectory produced by two x-ray beams spaced 360° apart, generated using a plurality of x-ray tubes, a multi-anode x-ray tube, or an axially extended-anode x-ray tube.

With continuing reference to FIG. 1 and with further reference to FIG. 4, increased scanning speed for another exemplary four-dimensional computed tomography imaging embodiment is obtained by using x-ray sources located at two axial positions. In the specific arrangement of FIG. 4, x-ray beams originating from two sources S1, S2 axially spaced along a line parallel to the axial or Z-direction direction are used. The x-ray sources S1, S2 can be a plurality of conventional x-ray tubes, anodes of a multiple-anode x-ray tube, axially spaced x-ray generation positions on an axially extended anode, or the like. For each angular viewing bin, projection data is collected for x-ray beams generated by each of the sources S1, S2.

FIG. 4 shows a two-turn helical trajectory acquired over a single 360° gantry rotation by simultaneously acquiring projection data produced by x-ray sources S1 and S2. The portion of the helix acquired using the source S1 is shown as a thick solid helical portion, while the portion of the helix acquired using the source S2 is shown as a thick dashed helical portion.

The x-ray sources S1, S2 are axially spaced at a distance corresponding to a linear distance that the subject support 16 moves over one 360° source rotation. Hence, after a 360° gantry rotation the source S1 is positioned at the initial position of the source S2 with respect to the volume of interest 46, and the helical turns acquired using each of the sources S1 and S2 combine to form the single two-turn helix that spans the volume of interest 46. A single gantry rotation provides 2×360°=720° of projection data for the two-turn helix since data is simultaneously acquired using two x-ray sources S1 and S2.

Since the two-turn helix corresponds to 720° of projection data in a single gantry rotation, the acquisition rate is effectively doubled. By adding additional sources spaced 360° apart, the acquisition rate can similarly be tripled, quadrupled, etc. by using three, four, etc. cooperating sources. For example, with four sources spaced at 360° intervals, a single gantry rotation will acquire 4×360°=1440° of angular data.

The approach of FIG. 4 retains mechanical relative motion between the x-ray sources and the couch, and hence fast retrace of the sources after each scan is difficult. Moreover, the joining of helices at 360° intervals introduces some complexities in image reconstruction since there is a temporal discontinuity at each joining point. This causes a discontinuity in the time skewing of the combined helix.

Figure 5B:
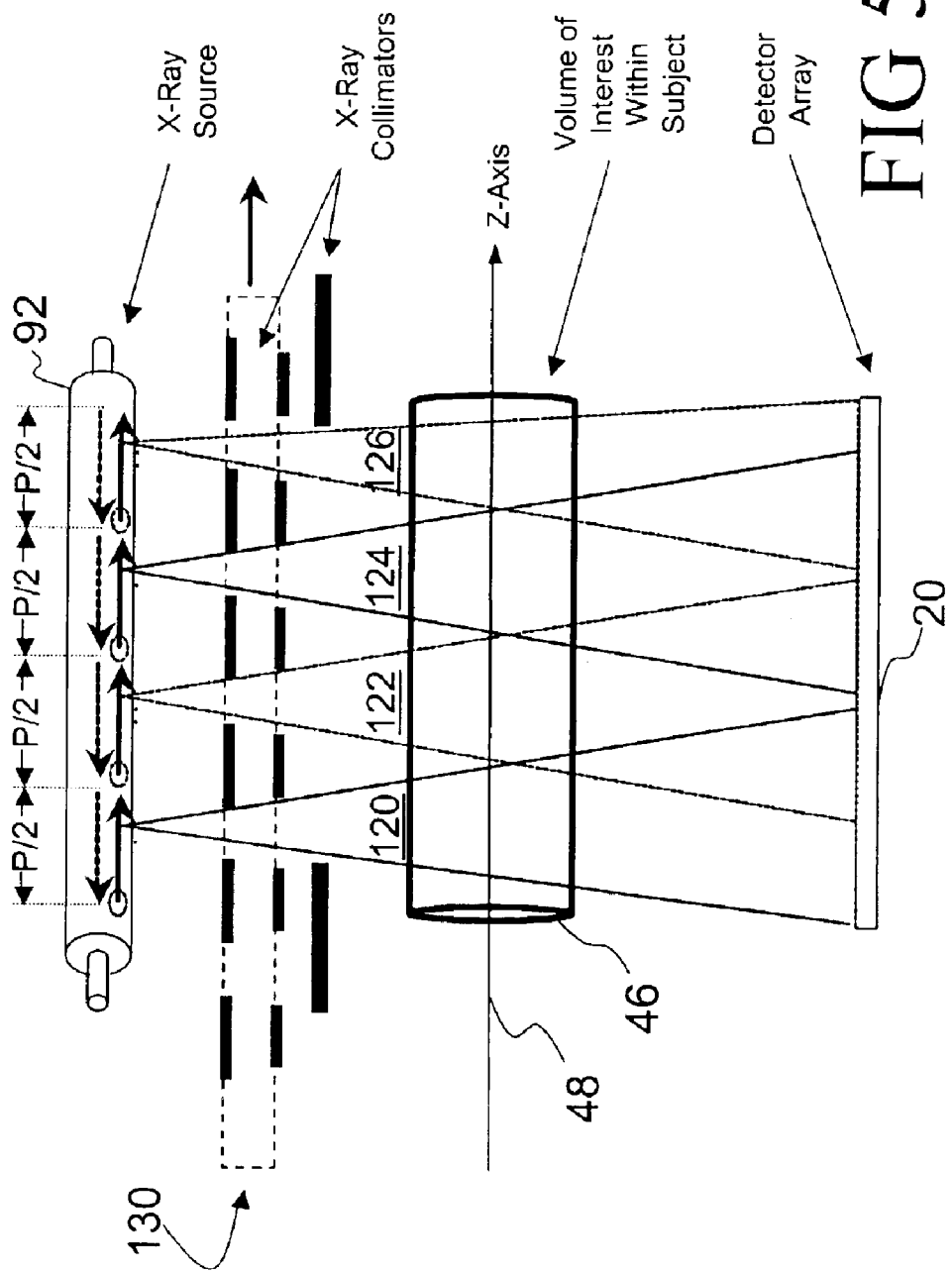
FIG. 5B shows a suitable x-ray beam collimation arrangement for four axially spaced x-ray beams produced by the x-ray tube of FIG. 5A.

With reference to FIGS. 5A and 5B, in an electronic embodiment the x-ray source 12 preferably includes a cylindrical anode 92 aligned along the axial or Z-direction that rotates 94. Other axially extended anode configurations can also be used. One or more electron accelerators $96_1$, $96_2$ produce one or more generally collimated electron beams that passes through an electrostatic beam deflector. The beam deflector includes electrostatic electrode elements 98, 100 coupled to the electron accelerators $96_1$, $96_2$, respectively, which is selectively axially deflect the electron beams. Instead of electrostatic beam deflectors, electromagnetic beam deflectors can be used.

A switch/sweep electronic controller 102 selectively switches between several selected electron beam trajectories 110, 112, 114, 116. Each of the electron beam trajectories 110, 112, 114, 116 strike the cylindrical anode 92 at predetermined axial locations to selectively produce one of several axially spaced conical- or wedge-shaped x-ray beams 120, 122, 124, 126. The switch/sweep electronic controller 102 additionally sweeps or shifts the electron beam trajectories 110, 112, 114, 116 axially across the anode (indicated by solid horizontal arrows in FIGS. 5A and 5B). The axial sweeping is substituted for axial movement of the subject support 16 which is used in conventional computed tomography imaging. The sweeping can be bi-directional (i.e., back-and-forth). Alternatively, a sweep in one direction (indicated by the solid horizontal arrows) is followed by a fast re-trace (indicated by dashed horizontal arrows in FIGS. 5A and 5B).

The rotation 94 distributes heat generation across a surface of the anode 92. Preferably, the cylindrical anode 92 is also actively cooled using water or another coolant fluid. The coolant fluid can be delivered into the cylindrical anode 92 (which is hollow in this internally cooled arrangement) or thermally coupled to the cylindrical anode 92 by hollow coolant lines, structures, or other shrouding disposed nearby. For example, a shroud 128 which receives coolant is disposed adjacent but displaced from the anode on a side opposite the side struck by the electron beam, and extends partially around the cylindrical anode. Preferably, the electron beams 110, 112, 114, 116 strike the cylindrical anode 92 at about a 45° angle relative to a surface normal of the anode 92. Thermal management is further enhanced by sweeping the beams 110, 112, 114, 116 across the anode 92.

Of course, greater or fewer than four x-ray beams can be generated along the cylindrical anode 92, limited by the electron beam spot size, an axial length of the cylindrical anode 92, and the like. The wedge-shaped x-ray beams 120, 122, 124, 126 should have widths such that they do not overlap at the x-ray detector 20, and this presents a further limitation on the number of beams. The x-ray tube 12 preferably can produce different numbers and axial spacings of x-ray beams and different beam sweep rates by selective configuring of the switch/sweep electronic controller 102. In one preferred embodiment, the cylindrical anode 92 has an axial length of about fifteen centimeters which corresponds to a length of a typical heart in the axial direction plus cone beam fan.

In one suitable exemplary arrangement, four x-ray beams 120, 122, 124, 126 are generated as shown in FIGS. 5A and 5B. The x-ray beams 120, 122 are generated by the first electron accelerator $96_1$. The x-ray beams 124, 126 are generated by the second electron accelerator $96_2$. The x-ray beams 120, 124 are generated together as shown in FIG. 5B. Collimators 130 restrict the x-ray beams 120, 124 to avoid overlap at the detector 20. Similarly, the x-ray beams 122, 126 are generated together as indicated in phantom in FIG. 5B. Collimators 130 restrict the x-ray beams 122, 126 to avoid overlap at the detector 20. Hence, the x-ray tube 12 in cooperation with the collimators 130 can alternate between the x-ray beams 120, 124 and the x-ray beams 122, 126 in alternating projection views, and so projection data can be acquired along two interlaced helices as the gantry rotates.

Figure 6B:
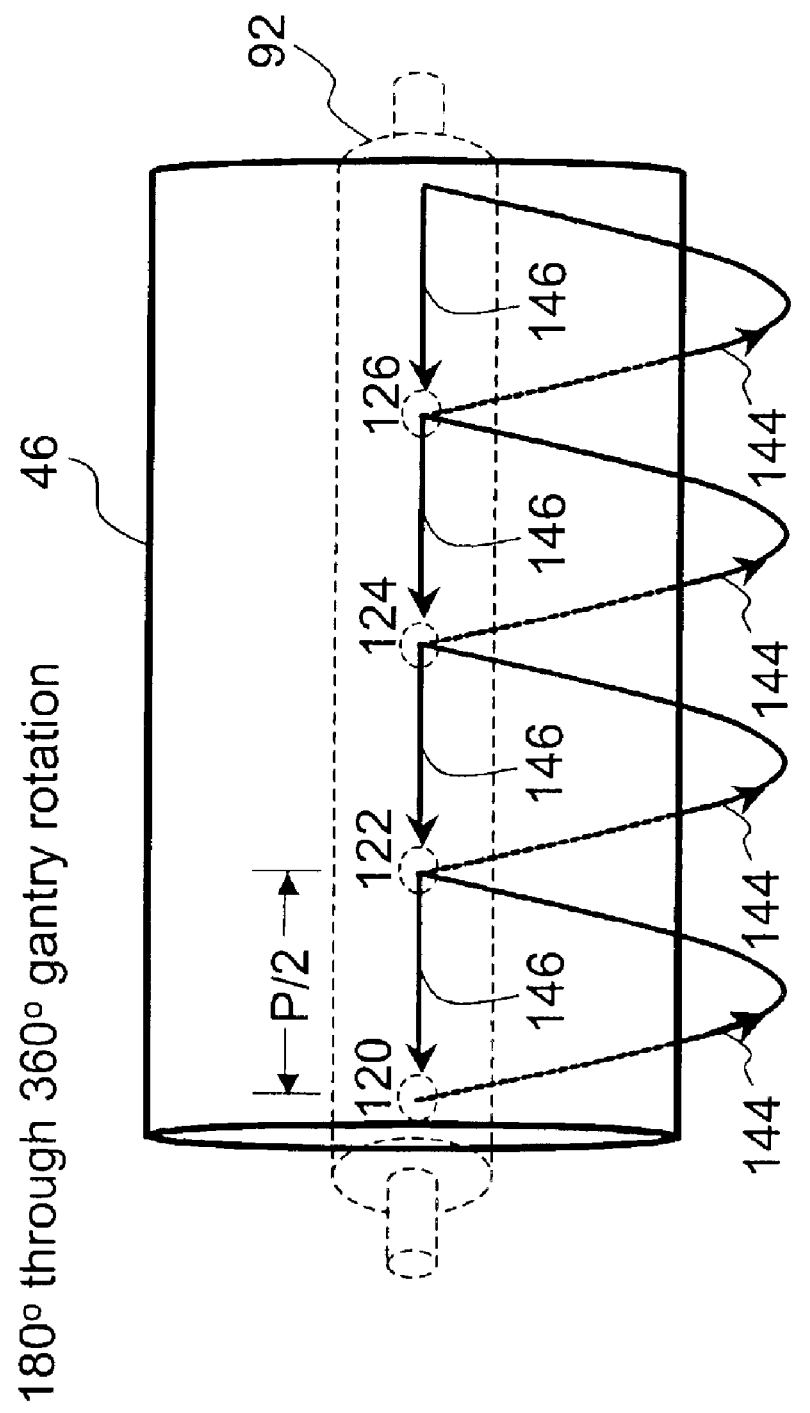
FIG. 6B shows second helical half-turns acquired during a second 180° gantry rotation following the first 180° gantry rotation of FIG. 5A.
Figure 7:
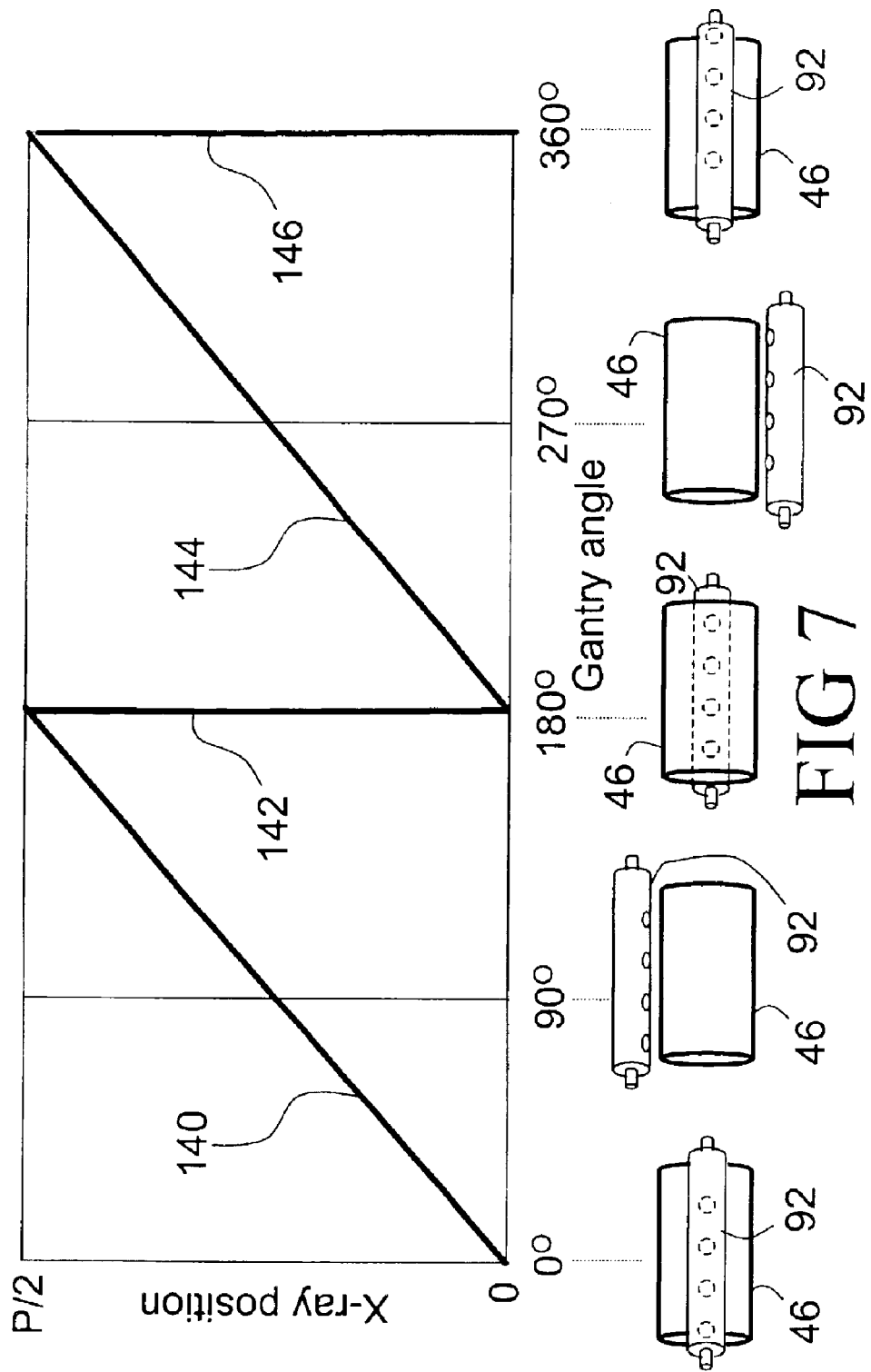
FIG. 7 plots the x-ray position on the anode for an arbitrary one of the electron beams of FIGS. 6A and 6B relative to an initial position of the beam. A corresponding arrangement of the anode and the volume of interest for the labeled gantry angles is schematically illustrated below each gantry angle label.

With continuing reference to FIGS. 1, 5A, and 5B, and with further reference to FIGS. 6A, 6B, and 7, the x-ray tube 12 provides for acquisition of two helices, namely helix I and helix II. In FIGS. 6A and 6B, portions of the helices lying in front of the region of interest 46 are represented by solid lines, while helix portions that pass behind the region of interest 46 are represented by dotted lines.

Trajectories of x-ray beams 120, 122, 124, 126 during gantry 18 rotation between 0° and 180° are shown in FIG. 6A. Trajectories of x-ray beams 120, 122, 124, 126 during gantry 18 rotation between 180° to 360° are shown in FIG. 6B. The anode 92 and a starting emission position for each of the x-ray beams 120, 122, 124, 126 on the anode 92 (the latter designated by open circles in FIGS. 6A and 6B) are indicated in phantom using thin dashed lines in FIGS. 6A and 6B. The x-ray beams 120, 122, 124, 126 sweep together across the anode 92.

FIG. 7 shows a plot of x-ray beam position (relative to the starting emission position) versus the gantry angular position. Moreover, for each of the labeled gantry positions 0°, 90°, 180°, 270°, 360°, a schematic representation of the position of the anode 92 with the x-ray beam generation positions relative to the volume of interest 46 is shown below the gantry angular label.

Unlike the previous embodiments, the electronic embodiment of FIGS. 6A, 6B, and 7 does not employ linear movement of the subject support 16 during the imaging. Rather, helical source trajectories are achieved by axially scanning the x-ray-generating electron beam paths 110, 112, 114, 116 along the anode 92 during rotation of the gantry 18. Each electron beam path 110, 112, 114, 116 moves from the starting emission position (indicated by the open circle) a distance P/2 between 0° and 180°, where P is the axial length of a full 360° turn of the helix. Correspondingly, each x-ray beam 120, 122, 124, 126 moves along a half-turn 140 of a helix of axial length P during the first 180° of rotation. The x-ray beams 120, 124 produce two half-turns 140 corresponding to helix I. The x-ray beams 122, 126 produce two half-turns 140 corresponding to helix II.

In a suitable timing sequence, in a first angular view the x-ray beams 120, 124 are operating to generate projection data for the helix I, while the x-ray beams 122, 126 are off. In the next adjacent angular view the x-ray beams 122, 126 are operating to generate projection data for the helix II, while the x-ray beams 120, 124 are off. As seen in FIG. 5A, this timing is suitably implemented using the cooperating electron accelerators $96_1$, $96_2$ and the beam deflectors 98, 100. Moreover, as seen in FIG. 5B the collimators 30 ensure that with this timing sequence there is no overlapping of operating x-ray beams.

At 180°, a fast retrace portion 142 returns the electron beams 110, 112, 114, 116 to the starting emission positions indicated by open circles. Each electron beam 110, 112, 114, 116 again moves from the starting emission position the distance P/2 between 180° and 360°, and correspondingly each x-ray beam 120, 122, 124, 126 moves along a second half-turn 144 of the helix and combine with half-turns 140 to complete full turns. The x-ray beams 122, 126 produce two half-turns 144 corresponding to helix I. The x-ray beams 120, 124 produce two half-turns 144 corresponding to helix II. At 360°, a second fast retrace portion 146 again returns the electron beams 110, 112, 114, 116 to the starting emission positions. The process is repeated for each 360° gantry rotation during imaging.

The fast retrace removes the temporal discontinuity at joining points of helix portions generated by different x-ray beams. However, optionally some overscan is performed to facilitate feathering of the cone beam projection data at the joining points.

Using the two interlaced helices I, II as shown in FIGS. 6–7, the entire volume of interest 46 is scanned in a single gantry rotation. A reduced sampling interval between acquisition of image representations of the volume of interest 46 of $T_{rot}/M$ is obtained where $T_{rot}$ is the time for a single rotation of the gantry 18 and x-ray source 12, and M is the number of x-ray beams. Hence, for the arrangement of FIGS. 6–7 the time interval between scans of the volume of interest 46 is $T_{rot}/4$. This results in a reduced time skew in each image representation of the volume of interest 46.

The sampling rate for the electronic embodiment described with particular reference to FIGS. 5–7 is substantially higher than that which is achieved using the mechanical embodiments of FIGS. 2–4. However, each of helix I and helix II will have some time skew. Hence, when using the electronic embodiment of FIGS. 5–7, the average voxel acquisition time values given in equations (3) and (4) are preferably computed by the voxel time processor 66 for each voxel of each reconstructed image. The voxel interpolator 68 suitably applies interpolation, curve fitting, or the like to determine a time-dependent value for each voxel in the region of interest 46.

Each voxel is sampled two times per gantry rotation: once by helix I, and once by helix II. For a rotation rate of, for example, 150 rpm, this means that each voxel is sampled every 200 milliseconds. For a heart rate of 75 beats per minute, the cardiac cycle period is 800 milliseconds, and so each voxel is sampled four times per cardiac cycle.

Figure 8A:
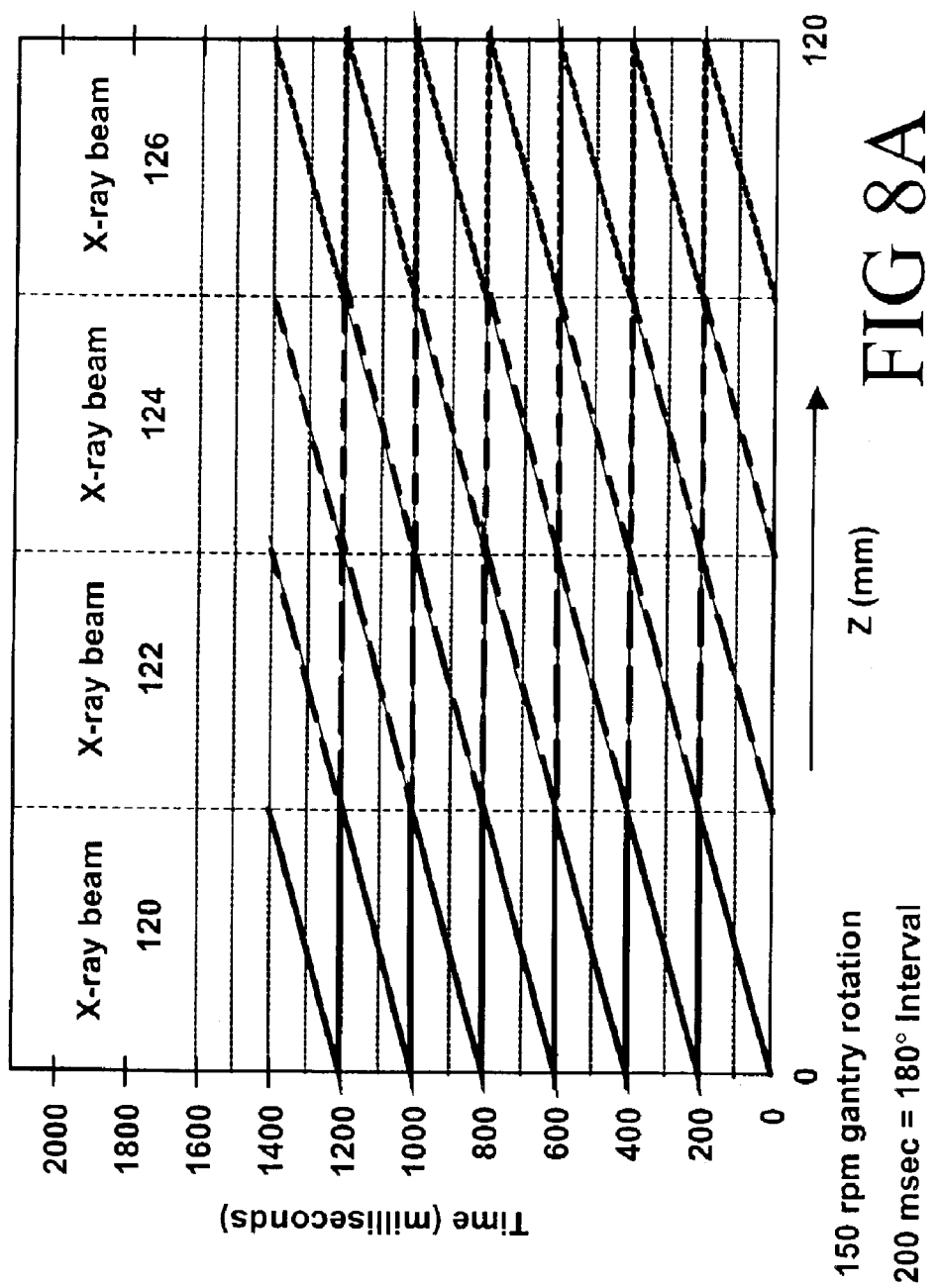
FIG. 8A shows a map of projection data acquisition time versus axial position for sampling performed using the electronically switched/swept x-ray beam embodiment of FIGS. 5–7.

With reference to FIG. 8A, voxel acquisition times for voxels lying on the central cylindrical axis 48 of the volume of interest 46 is shown. Data acquired using the x-ray beam 120 is shown by solid lines, data acquired using the x-ray beam 122 is shown by long dashed lines, data acquired using the x-ray beam 124 is shown by short dashed lines, and data acquired using the x-ray beam 126 is shown by dotted lines. For a 150 rpm gantry rotation the acquisition sequence of FIG. 8A samples each voxel every 200 milliseconds. In one data processing approach, voxel values are interpolated for times at 100 millisecond increments, as indicated by thin dotted horizontal lines. This provides eight samples per cardiac cycle for a heart rate of 75 beats per minute. The interpolated data provides a four-dimensional data set from which can be extracted anatomical portions at selected cardiac states or phases.

For the same timing as shown in FIG. 8A except at a rotation of 300 rpm, each voxel is sampled every 100 milliseconds, enabling interpolation at 50 millisecond increments to provide sixteen interpolated samples per cardiac cycle for a heart rate of 75 beats per minute. Because of this large number of samples per cardiac cycle, the imaging illustrated in FIG. 8A is optionally performed without cardiac gating via the electrocardiograph 30. Rather, the computed tomography images are acquired rapidly enough to provide interpolated cardiac phase resolution from which cardiac cycling information can be directly extracted. This direct approach is particularly beneficial for diagnosing an arrhythmic heart in which the cardiac cycle varies rapidly from heart beat to heart beat.

With reference to FIG. 8B, another imaging session is simulated, which employs the electronic embodiment of FIGS. 5–7 with cardiac gating and a 300 rpm gantry rotation. The four x-ray beams 120, 122, 124, 126 are swept forward twice for one phase, e.g. at end-systole, at around 200 milliseconds in exemplary FIG. 8B. The four x-ray beams 120, 122, 124, 126 are swept backward twice for a corresponding phase of diastasis, at around 600 milliseconds in exemplary FIG. 8B for a heart rate of about 75 beats per minute.

With returning reference to FIGS. 5A and 5B, the x-ray tube 12 which includes the elongated cylindrical anode 92 is particularly suitable for switched/sweeping beam imaging modes such as are described with reference to FIGS. 6–8. However, the x-ray tube 12 of FIGS. 5A and 5B can also perform conventional single-spot computed tomography by omitting switching of the electron beam along the cylindrical anode 92. Hence, for example, the single-spot imaging trajectories shown in FIG. 2 can be acquired using the x-ray tube 12 of FIG. 5 by configuring the controller 102 to produce a single unswitched x-ray beam. However, in such a single-beam mode the anode 92 can be substantially heated at the fixed x-ray generation spot. Hence, for the single-spot imaging trajectories shown in FIG. 2 a conventional x-ray tube may be preferable.

Similarly, the x-ray tube 12 of FIG. 5 can be used to perform a single helical scan over one or more gantry rotations by sweeping a single electron beam axially across the anode 92. Hence, conventional helical conebeam computed tomography imaging can be performed using the x-ray tube 12 without linear motion of the subject support 16.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A helical cone beam computed tomography imaging apparatus comprising:

means for acquiring helical cone beam computed tomography projection data for a volume of interest using a plurality of source trajectory helices that temporally overlap, each source trajectory helix being triggered based on detection of a selected cardiac phase, the selected triggering cardiac phase being different for each helix;

means for reconstructing the acquired helical cone beam computed tomography projection data for each helix to generate a corresponding time skewed volume image representation of the volume of interest, the time skewed volume image representations temporally overlapping due to the temporal overlap of the source trajectory helices;

means for computing a voxel acquisition time for each voxel for each time skewed volume image representation; and means for computing an interpolated voxel value for each voxel based on values of the voxel in the plurality of image representations and corresponding voxel acquisition times.

2. The imaging apparatus as set forth in claim 1, wherein the volume of interest undergoes a cyclical temporal variation, and each source trajectory helix spans the volume of interest over a time interval less than one cycle period of the cyclical temporal variation of the volume of interest.

3. The imaging apparatus as set forth in claim 1, wherein the computing of a voxel acquisition time for each voxel of each time skewed volume image representation includes:
computing the voxel acquisition time as a time average of the contiguous acquisition time interval corresponding to the voxel.

4. The imaging apparatus as set forth in claim 1, wherein the computing of an interpolated voxel value includes:
for each voxel, computing a time-dependent voxel value based on values of the voxel in the plurality of time skewed volume image representations and corresponding voxel acquisition times.

5. A helical cone beam computed tomography imaging method comprising:
acquiring helical cone beam computed tomography projection data for a volume of interest using a plurality of source trajectory helices;
reconstructing the acquired helical cone beam computed tomography projection data for each helix to generate a corresponding time skewed volume image representation of the volume of interest, each voxel being reconstructed based on projection data acquired over a single contiguous acquisition time interval of the corresponding source trajectory helix;
for each time skewed volume image representation, computing a voxel acquisition time for each voxel by:
identifying a PI line associated with the voxel;
determining a PI line time interval corresponding to the PI line; and
computing the voxel acquisition time as a statistical characteristic time value of the PI line time interval; and
for each voxel, computing an interpolated voxel value based on values of the voxel in the plurality of image representations and corresponding voxel acquisition times.

6. The imaging method as set forth in claim 5, wherein time intervals between voxel acquisition times for at least some voxels are less than a time interval over which a helix is acquired.

7. The imaging method as set forth in claim 5, wherein the acquiring of helical cone beam computed tomography projection data for a volume of interest using a plurality of source trajectory helices includes:
for each helix, acquiring generally non-overlapping projection views during adjacent helical turns.

8. The imaging method as set forth in claim 5, wherein at least some of the plurality of source trajectory helices span less than the entire volume of interest.

9. The imaging method as set forth in claim 5, wherein the acquiring of helical cone beam computed tomography projection data for a volume of interest using a plurality of source trajectory helices includes:
rotating a radiation source about the volume of interest; and
simultaneously with the rotating, cyclically relatively axially moving the volume of interest and the radiation source.

10. The imaging method as set forth in claim 9, wherein the acquiring of helical cone beam computed tomography projection data for a volume of interest using a plurality of source trajectory helices includes:
during the simultaneous rotating and relative axial moving, acquiring projection data using a plurality of axially spaced radiation cone beam source positions.

11. The imaging method as se forth in claim 5, wherein the volume of interest includes a cyclically temporally varying organ an the computing of an interpolated voxel value includes:
interpolating voxels of the time skewed volume image representations that have voxel acquisition times corresponding to a selected state of the cyclically temporally varying organ.

12. A helical cone beam computed tomography imaging method comprising:
rotating a cone beam radiation source about a volume of interest;
simultaneously with the rotating, axially sweeping an electron beam parallel to an axis of radiation source rotation across an axially elongated anode of the radiation source, the electron beam defining an x-ray cone beam generation position on the anode, the rotating and the axial sweeping cooperating to generate the source trajectory helices about the volume of interest;
reconstructing the acquired helical cone beam computed tomography projection data for each helix to generate a corresponding time skewed volume image representation of the volume of interest; and
for each time skewed volume image representation, computing a voxel acquisition time for each voxel.

13. The imaging method as set forth in claim 12, wherein the acquiring of helical cone beam computed tomography projection data for a volume of interest using a plurality of source trajectory helices further includes:
fast re-tracing the electron beam between source trajectory helices.

14. The imaging method as set forth in claim 12, wherein the axial sweeping includes simultaneously axially sweeping at least two x-ray cone beam generation positions across the axially elongated anode.

15. The imaging method as set forth in claim 12, wherein the volume of interest is a cardiac region and the acquiring of helical cone beam computed tomography projection data for the volume of interest using a plurality of source trajectory helices includes:
triggering each source trajectory helix based on detection of a selected cardiac phase.

16. The imaging method as set forth in claim 12, further comprising:
keeping the volume of interest stationary during the rotating of the cone beam radiation source and the sweeping of the electron beam across the axially elongated anode of the radiation source.

17. A cardiac helical cone beam computed tomography imaging method comprising:
acquiring helical cone beam computed tomography projection data for a volume of interest using a plurality, of source trajectory helices, each source trajectory being triggered based on detection of a selected cardiac phase, the selected triggering cardiac phase being different for each helix;
reconstructing the acquired helical cone beam computed tomography projection data for each helix to generate a corresponding time skewed volume image representation of the volume of interest;
for each time skewed volume image representation, computing a voxel acquisition time for each voxel; and
for each voxel, computing an interpolated voxel value based on values of the voxel in the plurality of image representations and corresponding voxel acquisition times.

18. A cardiac helical cone beam computed tomography imaging method comprising:
   acquiring helical cone beam computed tomography projection data for a volume of interest using a plurality of source trajectory helices, each source trajectory being triggered based on detection of a selected cardiac phase, at least two source trajectory helices being triggered within a single cardiac cycle;
   reconstructing the acquired helical cone beam computed tomography projection data for each helix to generate a corresponding time skewed volume image representation of the volume of interest;
   for each time skewed volume image representation, computing a voxel acquisition time for each voxel; and
   for each voxel, computing an interpolated voxel value based on values of the voxel in the plurality of image representations and corresponding voxel acquisition times.

19. An apparatus for performing helical cone beam computed tomography imaging, the apparatus comprising:
   a means for acquiring helical cone beam computed tomography projection data for a volume of interest using a plurality of source trajectory helices, each source trajectory helix being triggered based on detection of a selected cardiac phase, at least two source trajectory helices being triggered within a single cardiac cycle;
   a means for triggering the acquiring of conebeam projection data starting at points in a physiological cycle which vary among the trajectory helices;
   a means for reconstructing the acquired helical cone beam computed tomography projection data for each helix to generate a corresponding time skewed volume image representation of the volume of interest;
   a means for computing a voxel acquisition time for each voxel of each time skewed image representation; and.
   a means for computing an interpolated voxel value for each voxel based on values of the voxel in the plurality of time skewed image representations and corresponding voxel acquisition times.

20. The apparatus as set forth in claim 19, wherein the means for acquiring helical cone beam computed tomography projection data includes:
   a rotating gantry;
   an x-ray source arranged on the rotating gantry, the x-ray source rotating with the rotating gantry and producing an x-ray cone beam that passes through the volume of interest;
   a radiation detector arranged to detect x-rays produced by the x-ray cone beam source after passing through the volume of interest;
   a support structure that supports an imaging subject, at least a portion of which imaging subject defines the volume of interest; and
   a means for relatively axially moving the support structure and the x-ray cone beam, the axial moving cooperating with rotating of the gantry to produce the source trajectory helices.

21. The apparatus as set forth in claim 19, wherein the means for computing an interpolated voxel value for each voxel includes:
   computing a time-dependent voxel value based on the values of the voxel in the plurality of time skewed volume image representations and corresponding voxel acquisition times.

22. An apparatus for performing helical cone beam computed tomography imaging, the apparatus comprising:
   a means for triggering the acquiring of conebeam projections data for a volume of interest starting at points in a physiological cycle which vary among a plurality of trajectory helices;
   a means for acquiring helical cone beam computed tomography projection data responsive to the triggering, the acquiring means including: (i) a rotating gantry, (ii) an x-ray source arranged on the rotating gantry including an axially extended anode and an electron source that axially sweeps an electron beam along the anode to produce an axially sweeping x-ray cone beam in coordination with the triggering means, the axial sweeping cooperating with rotating of the gantry to produce the source trajectory helices, (iii) a radiation detector arranged to detect x-rays produced by the x-ray source after passing through the volume of interest, and (iv) a support structure that supports an imaging subject, at least a portion of which imaging subject defines the volume of interest;
   a means for reconstructing the acquired helical cone beam computed tomography projection data for the helixes to generate a corresponding time skewed image representations of the volume of interest;
   a means for computing voxel acquisition times for the voxels of the time skewed image representations; and
   a means for computing interpolated voxel values for selected voxels based on values of the corresponding voxel the time skewed image representations and corresponding voxel acquisition times.

23. The apparatus as set forth in claim 22, further including:
   a beam-switching means for switching the sweeping electron beam between a plurality of axially spaced positions on the anode to produce a plurality of axially spaced sweeping x-ray cone beams.

24. The apparatus as set forth in claim 22, wherein the volume of interest includes at least a portion of the heart, and the means for acquiring helical cone beam computed tomography projection data for a volume of interest using a plurality of source trajectory helices includes:
   an electrocardiograph that triggers the source trajectory helices.

25. The apparatus as set forth in claim 24, wherein the means for computing an interpolated voxel value includes:
   selecting voxel values from the time skewed volume image representations whose corresponding voxel acquisition times correspond to an occurrence of one of a selected cardiac phase and a selected state of cardiac motion; and
   combining the selected voxel values to generate an image representation of the selected cardiac phase or selected state of cardiac motion.

26. An apparatus for performing high-speed computed tomography imaging, the apparatus comprising:
   a rotating gantry;
   an x-ray source disposed on the rotating gantry and rotating therewith, the x-ray source including an axially oriented cylindrical anode, an electron source irradiating the cylindrical anode to produce an x-ray beam traversing a volume of interest, and an electron beam deflector that axially deflects the electron beam along the cylindrical anode to axially sweep the x-ray beam, a period of the axial sweep of the x-ray beam along the cylindrical anode being coordinated to a period of rotation of the rotating gantry to produce a helical trajectory of the x-ray beam about the volume of interest;

a radiation detector arranged to measure the x-ray beam after passing through the volume of interest; and a reconstruction processor that reconstructs the acquired projection data to produce a time skewed image representation corresponding to the helical trajectory.

27. The apparatus as set forth in claim 26, wherein the electron beam deflector switches the electron beam between at least two axially spaced positions on the anode, the at least two axially spaced positions selected to define at least two helical trajectories each spanning a portion of the volume of interest and arranged to cooperatively define a helical trajectory spanning the volume of interest.

28. The apparatus as set forth in claim 26, wherein the electron beam deflector switches the electron beam between at least two axially spaced positions on the anode, the at least two axially spaced positions selected to define at least two interlaced helical trajectories.

29. In a conebeam helical computed tomography imaging system including a rotating gantry and a means for controlling sweeping of an x-ray tube electron beam in accordance with rotation of the gantry, an x-ray tube comprising:

a cylindrical anode whose cylindrical axis is axially oriented with respect to a rotation axis of the rotating gantry;

an electron source that produces an electron beam generally directed toward the cylindrical anode, which electron beam interacts with the cylindrical anode to produce a cone beam of x-rays; and an electron beam deflector that sweeps the electron beam axially across the cylindrical anode;

wherein a ratio of a sweep speed of the electron beam to a rotation rate of the rotating gantry being selected to generate a selected helical trajectory of the cone beam about a region of interest.

\* \* \* \* \*